(12) United States Patent
Teshigawara et al.

(10) Patent No.: US 11,244,480 B2
(45) Date of Patent: Feb. 8, 2022

(54) MEDICAL INFORMATION PROCESSING APPARATUS

(71) Applicant: Canon Medical Systems Corporation, Otawara (JP)

(72) Inventors: Manabu Teshigawara, Otawara (JP); Takahiro Yoda, Nasushiobara (JP); Ryo Okuda, Utsunomiya (JP); Hiroki Tawara, Tokyo (JP)

(73) Assignee: Canon Medical Systems Corporation, Otawara (JP)

( * ) Notice: Subject to any disclaimer, the term of this patent is extended or adjusted under 35 U.S.C. 154(b) by 120 days.

(21) Appl. No.: 16/451,207

(22) Filed: Jun. 25, 2019

(65) Prior Publication Data

US 2020/0005495 A1 Jan. 2, 2020

(30) Foreign Application Priority Data

Jun. 29, 2018 (JP) ................................ 2018-124773

(51) Int. Cl.
| | |
|---|---|
| *G06T 11/00* | (2006.01) |
| *G16H 30/40* | (2018.01) |
| *A61B 5/00* | (2006.01) |
| *A61B 6/00* | (2006.01) |
| *G16H 50/20* | (2018.01) |

(52) U.S. Cl.
CPC .......... *G06T 11/005* (2013.01); *A61B 5/7267* (2013.01); *A61B 6/4258* (2013.01); *G16H 30/40* (2018.01); *G16H 50/20* (2018.01); *G06T 2210/41* (2013.01)

(58) Field of Classification Search
None
See application file for complete search history.

(56) References Cited

U.S. PATENT DOCUMENTS

| | | | |
|---|---|---|---|
| 9,128,193 B2 | 9/2015 | Wang et al. | |
| 2004/0210132 A1* | 10/2004 | Manjeshwar | G01T 1/2018 |
| | | | 600/436 |
| 2005/0151084 A1 | 7/2005 | Zibulevsky et al. | |
| 2015/0276953 A1 | 10/2015 | Espana Palomares | |
| 2018/0144465 A1* | 5/2018 | Hsieh | G06N 3/08 |
| 2018/0197317 A1* | 7/2018 | Cheng | G06N 3/08 |
| 2019/0104940 A1* | 4/2019 | Zhou | A61B 5/0073 |
| 2019/0251713 A1* | 8/2019 | Chen | G06N 3/084 |

(Continued)

OTHER PUBLICATIONS

Yang, Bao, Leslie Ying, and Jing Tang. "Enhancing Bayesian PET image reconstruction using neural networks." 2017 IEEE 14th International Symposium on Biomedical Imaging (ISBI 2017). IEEE, 2017. (Year: 2017).*

(Continued)

*Primary Examiner* — Samah A Beg
(74) *Attorney, Agent, or Firm* — Oblon, McClelland, Maier & Neustadt, L.L.P.

(57) ABSTRACT

According to one embodiment, a medical information processing apparatus includes processing circuitry. The processing circuitry is configured to receive data acquired by scan for an object, and output a reconstructed image data based on the data and a trained model that accepts the data as input data and outputs the reconstructed image data corresponding to the data. The trained model is trained by learning using raw data generated based on a numerical phantom and the numerical phantom.

10 Claims, 12 Drawing Sheets

(56) References Cited

U.S. PATENT DOCUMENTS

| | | | | |
|---|---|---|---|---|
| 2019/0287674 A1* | 9/2019 | Nitta | ................... | G06N 3/0454 |
| 2019/0355114 A1* | 11/2019 | Muehlberg | ............... | G06T 7/11 |
| 2019/0365341 A1* | 12/2019 | Chan | ................... | G06T 7/0012 |
| 2020/0034999 A1* | 1/2020 | Heteren | ............... | A61B 6/4452 |
| 2020/0065969 A1* | 2/2020 | Huang | ............... | G06N 3/0454 |
| 2020/0160509 A1* | 5/2020 | Pack | ................... | G16H 30/40 |
| 2021/0074036 A1* | 3/2021 | Fuchs | ................... | G06T 9/002 |

OTHER PUBLICATIONS

Bevilacqua, A., et al. "A new approach to positron emission tomography (PET) image reconstruction using artificial neural networks (ANN)." Int. J. Mod. Phys. C 9.1 (1998): 71-85. (Year: 1998).*

Shen, Chenyang, et al. "Intelligent parameter tuning in optimization-based iterative CT reconstruction via deep reinforcement learning." IEEE transactions on medical imaging 37.6 (2018): 1430-1439. (Year: 2018).*

Xu, Qiong, et al. "Low-dose X-ray CT reconstruction via dictionary learning." IEEE transactions on medical imaging 31.9 (2012): 1682-1697. (Year: 2012).*

Paschalls, P. et al. "Tomographic image reconstruction using Artificial Neural Networks", Nuclear Instruments and Methods in Physics Research A 527, 2004, pp. 211-215.

Wuerfl, T. et al. "Deep Learning Computed Tomography", Medical Image Computing and Computer-Assisted Intervention (MICCAI), 2016, pp. 432-440.

\* cited by examiner

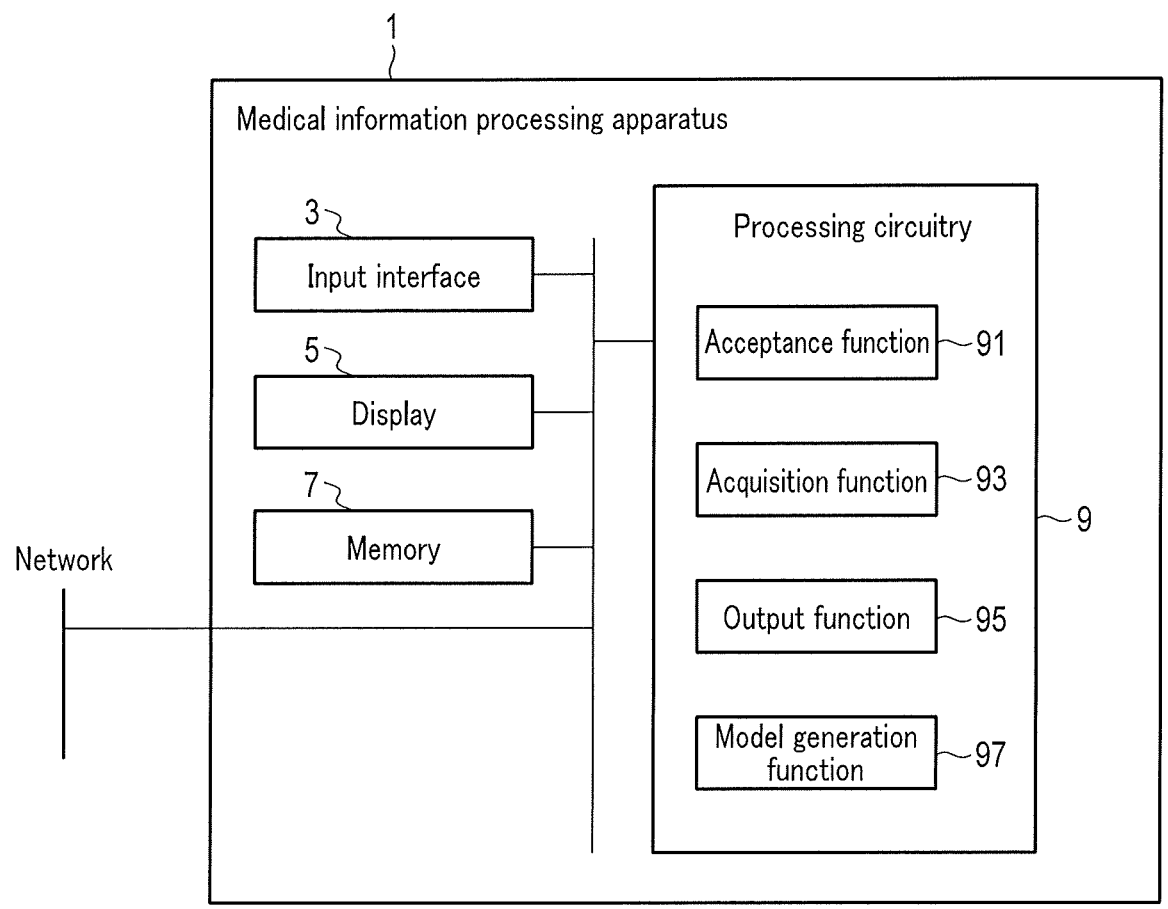
F I G. 1

Numerical phantom

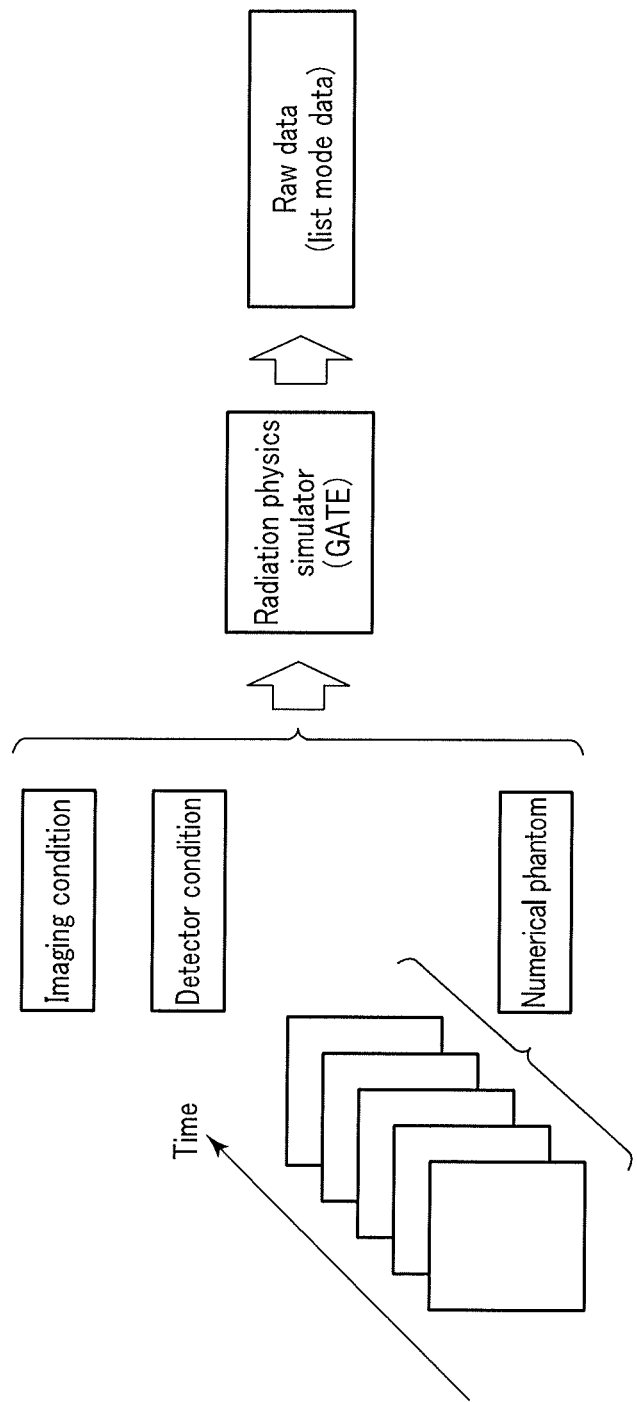
F I G. 4

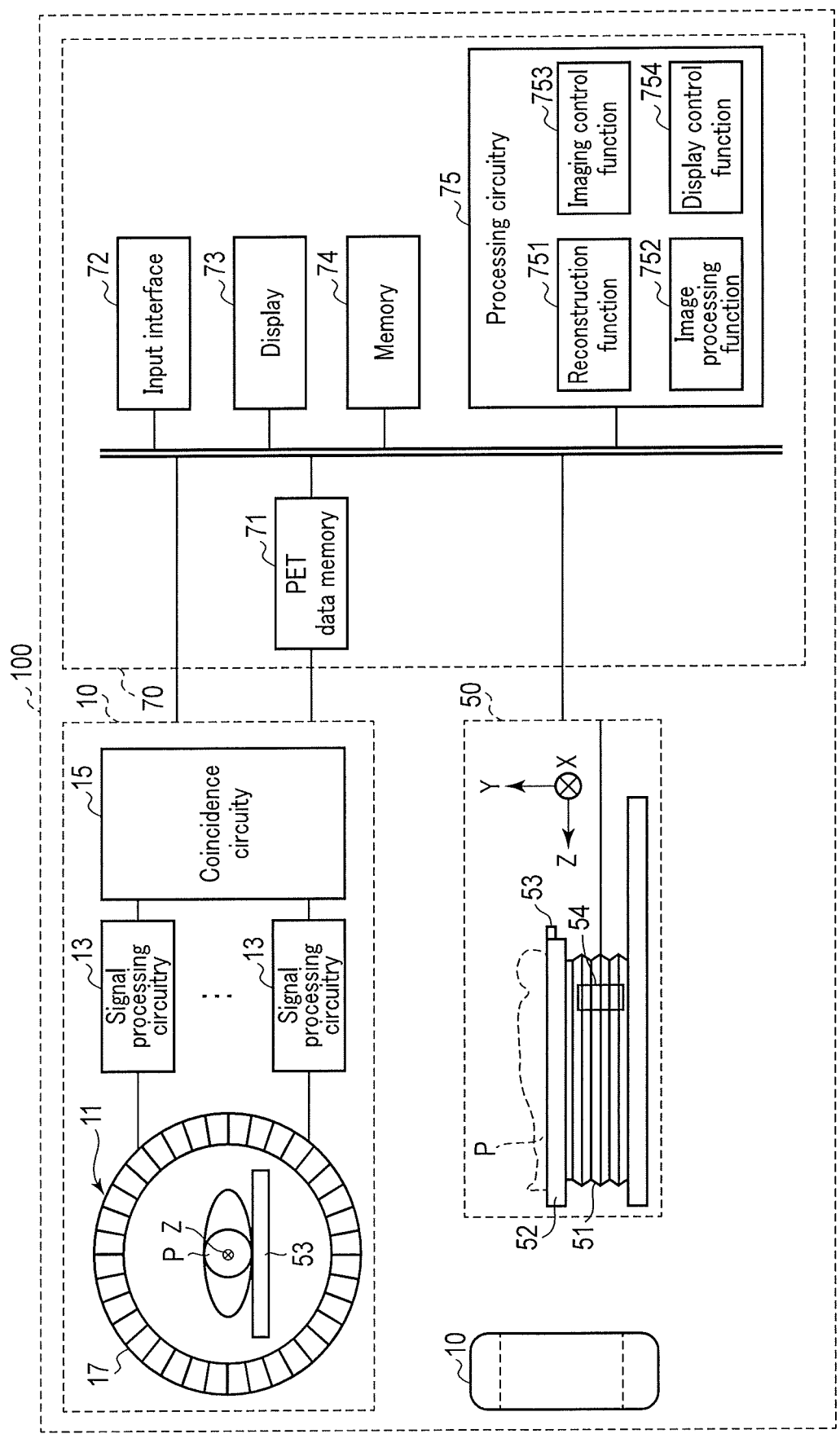
F I G. 9

MEDICAL INFORMATION PROCESSING APPARATUS

CROSS-REFERENCE TO RELATED APPLICATIONS

This application is based upon and claims the benefit of priority from the prior Japanese Patent Application No. 2018-124773, filed Jun. 29, 2018, the entire contents of which are incorporated herein by reference.

FIELD

Embodiments described herein relate generally to a medical information processing apparatus.

BACKGROUND

In general, a PET (Positron Emission Tomography) apparatus obtains a reconstructed image from raw data of gamma ray detection acquired by a detector using an FBP (Filtered Back-projection) method, an ML-EM (Maximum Likelihood Expectation-Maximization) method, or the like. In recent years, methods have been studied in which the quality of a reconstructed image is improved by applying a noise reduction filter using a DCNN (Deep Convolutional Neural Network) to the reconstructed image, or applying a filter using the DCNN and configured to improve the spatial resolution to the reconstructed image. In addition, a method has been studied in which whole image reconstruction processing for obtaining a reconstructed image is executed using a neural network. These methods are applied to, for example, reconstruction processing of a PET apparatus. In these methods, learning of a neural network is needed to make an input image input to the DCNN close to an ideal image. To learn the neural network, an ideal image serving as teaching data is necessary.

However, to acquire an ideal image serving as teaching data by actual PET scan, it is necessary to administer an enormous amount of radiopharmaceutical to an object (patient) and increase the count of photons in raw data as much as possible. In fact, from the viewpoint of exposure, it is difficult to execute PET scan in a state in which an enormous amount of radiopharmaceutical is administered to the object. In addition, if the count is increased as much as possible by long time acquisition using a normal administration amount of radiopharmaceutical, an ideal image cannot be obtained because of a blur caused by the body motion of the object. Furthermore, although the image used for learning of DCNN has temporarily been called an "ideal image" above, an image acquired by an finite administration amount and a finite count inevitably has a statistical fluctuation caused by a quantal phenomenon. For this reason, the acquired image is strictly not an ideal image.

BRIEF DESCRIPTION OF THE DRAWINGS

FIG. 1 is a block diagram showing an example of the arrangement of a medical information processing apparatus according to the first embodiment;

FIG. 4 is a view showing an example of the outline of using a plurality of numerical phantoms along the time series in the training data generation processing in the first embodiment;

FIG. 9 is a view showing an example of the arrangement of a positron emission tomography (PET) apparatus in the first application example of the second embodiment;

DETAILED DESCRIPTION

Figure 2:
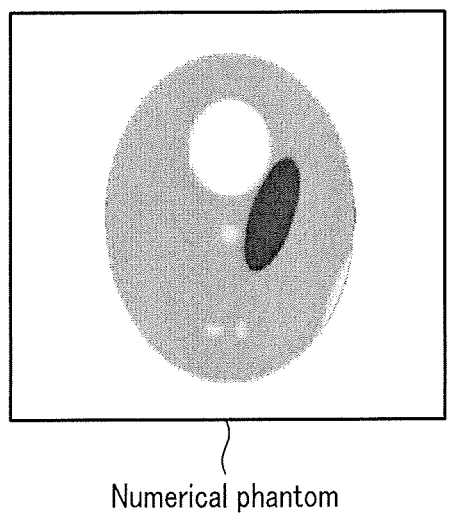
FIG. 2 is a view showing an example of a numerical phantom used for PET reconstruction learning in the first embodiment.

According to one embodiment, a medical information processing apparatus includes processing circuitry. The processing circuitry receives data acquired by scan of an object, and outputs a reconstructed image data based on a trained model that accepts the data as input data and outputs a reconstructed image data corresponding to the data. The trained model is trained by learning using raw data generated based on a numerical phantom and the numerical phantom.

It is an object to perform reconstruction processing in accordance with a trained model learned using raw data generated based on a numerical phantom and the numerical phantom.

A medical information processing apparatus according to an embodiment will now be described with reference to the accompanying drawings. First, in the first embodiment concerning the medical information processing apparatus, generation of training data to be used in learning of a machine learning model and learning of the machine learning model using the generated training data will be described. Next, in the second embodiment, a medical image diagnosis apparatus including a medical information processing apparatus configured to generate a reconstructed image using a learned machine learning model (to be referred to as a trained model hereinafter) will be described. The trained model is a machine learning model to which a function is imparted to accept data acquired by imaging (scan) of an object and output a reconstructed image data concerning the data.

The trained model is a learned machine learning model obtained by performing, by a model learning program, machine learning for a machine learning model before learning based on training data. The trained model receives acquired data and outputs a reconstructed image data. The trained model is a composite function with parameters in which a plurality of functions are composited. The composite function with parameters is defined by a combination of a plurality of adjustable functions and parameters (weights). The machine learning model according to this embodiment may be any composite function with parameters, which satisfies the above-described requirement. The machine learning model according to this embodiment is, for example, a multilayer network model (to be referred to as a multilayer network hereinafter).

A trained model using a multilayer network is, for example, a DNN (Deep Neural Network) that is a multilayer network as the target of deep learning. Note that as the DNN, for example, a CNN (Convolutional Neural Network) may be used. The DNN includes an input layer that receives data obtained by imaging an object, an output layer that outputs a reconstructed image data, and at least one intermediate layer provided between the input layer and the output layer. The trained model is used as, for example, a program module that is a part of artificial intelligence software.

The trained model and the training data change depending on the type of medical image diagnosis apparatus including the medical information processing apparatus that generates a reconstructed image data. The types of medical image diagnosis apparatus are, for example, a PET apparatus that executes PET (Positron Emission Tomography) imaging (PET scan), an X-ray CT apparatus that executes CT (Computed Tomography) scan, an SPECT apparatus that executes SPECT (Single Photon Emission CT) imaging (scan), a PET/CT apparatus, a PET/MR (Magnetic resonance Imaging) apparatus, an SPECT/CT apparatus, an SPECT/MRI apparatus, and the like.

First Embodiment

An object of this embodiment is t in acquiring training data, generate raw data for learning by a radiation physics simulation using a numerical phantom corresponding to a true ideal image without acquiring an ideal image serving as teaching data by actual PET imaging (PET scan) or CT scan. In the radiation physics simulation, examples of radiation are gamma rays and X-rays. Additionally, another object of this embodiment is to generate a trained model by learning a machine learning model by incorporating correction concerning generation of a reconstructed image using generated training data.

FIG. 1 is a block diagram showing an example of the arrangement of a medical information processing apparatus 1 according to the first embodiment. As shown in FIG. 1, the medical information processing apparatus 1 includes an input interface (input unit) 3, a display 5 (display unit), a memory (storage unit) 7, and processing circuitry (processing unit) 9. To make a detailed description, a case in which training data generated according to the embodiment is used in learning (to be referred to as PET reconstruction learning hereinafter) of a machine learning model used to generate a trained model to be used to reconstruct a PET image will be described as an example.

The input interface 3 accepts various kinds of input operations from an operator. The input interface 3 converts an accepted input operation into an electrical signal. The input interface 3 outputs the converted electrical signal to the processing circuitry 9. As the input interface 3, for example, a mouse, a keyboard, a track ball, a switch, a button, a joystick, a touch pad, a touch panel display, and the like can appropriately be used. Note that the input interface 3 is not limited to interfaces including a physical operation component such as a mouse, a keyboard, a track ball, a switch, a button, a joystick, a touch pad, and a touch panel display. For example, electrical signal processing circuitry configured to receive an electrical signal corresponding to an input operation from an external input device provided independently of the medical information processing apparatus 1 and output the electrical signal to the processing circuitry 9 is also included in the example of the input interface 3. In addition, the input interface 3 may be formed by a tablet terminal or the like which wirelessly communicate with the medical information processing apparatus 1.

The input interface 3 inputs various kinds of conditions to be input to a program (to be referred to as a radiation physics simulator hereinafter) concerning a radiation physics simulation. More specifically, the input interface 3 inputs an imaging condition (to be also referred to as a scan condition) and a detector condition. The imaging condition includes, for example, at least one of the count of gamma rays, the count rate of gamma rays, a radioisotope (to be referred to as RI hereinafter) name (nuclide name), and the like. The count of gamma rays corresponds to, for example, the acquisition time of acquired data. The count rate is, for example, a count per unit time according to the characteristic of an actual apparatus (medical image diagnosis apparatus) such as a count loss caused by pileup or the like. Note that the half-life of an RI or the like may be used in place of the RI name.

Note that if training data output in the medical information processing apparatus 1 is used for learning (to be referred to as CT reconstruction learning hereinafter) of a machine learning model used to generate a trained model used to reconstruct a CT image, the imaging condition (scan condition) includes, for example, at least one of a scan method concerning acquisition of data, such as helical scan or step & shoot scan, the number of views used to reconstruct a CT image, a tube voltage, and a tube current.

The detector condition is, for example, a condition concerning a plurality of detectors in the medical image diagnosis apparatus used in imaging (scan) of the object. The detector condition includes, for example, at least one of the radiation detection characteristic of each of the plurality of detectors, the gap (to be referred to as a detector gap hereinafter) between adjacent detectors in the plurality of detectors, and the geometrical arrangement of the plurality of detectors. The detector is, for example, a detector formed by combining a scintillator and a photomultiplier, an SiPM (Silicon Photomultiplier) detector, a semiconductor detector, or the like. The geometrical arrangement is, for example, a ring shape, an elliptical shape, a triangular shape, or the like.

A plurality of imaging conditions of different counts, count rates, RI names, and the like may be set in advance based on examination contents. In addition, a plurality of detector conditions of different detection characteristics, detector gaps, and geometrical arrangements may be set in advance based on the specifications of the medical image diagnosis apparatus. In these cases, the plurality of imaging conditions and the plurality of detector conditions are stored in the memory 7 in advance. Note that examination contents may be attached to the imaging condition. In these cases, the input interface 3 may input a selection instruction by the operator for the plurality of imaging conditions and the plurality of detector conditions displayed on the display 5. The selected imaging condition and detector condition are read from the memory 7 in response to the input of the selection instruction and output to the processing circuitry 9.

Note that the input interface 3 may input selection of hyperparameters. The hyperparameters are parameters set in advance before learning in the machine learning model before learning. The hyperparameters are, for example, the number of layers in the neural network, the number of units, the coefficients of regularization, and the like. The hyperparameters are associated with, for example, the quality of a reconstructed image generated by the trained model. In other words, the hyperparameters are associated with the application purpose of the reconstructed image such as diagnosis or imaging confirmation.

The display 5 displays various kinds of information under the control of the processing circuitry 9. For example, the display 5 displays a graphical user interface (to be referred to as a GUI hereinafter) concerning input of selection of the above-described various kinds of conditions and the hyperparameters. Note that the input screen displayed on the display 5 is not limited to the GUI. As the display 5, various arbitrary displays can appropriately be used. For example, as the display 5, a liquid crystal display, a CRT display, an organic EL display, or a plasma display can be used. In addition, the display 5 may be of a desktop type, or may be formed by a tablet terminal or the like capable of wirelessly communicating with the medical information processing apparatus 1.

The memory 7 is a storage device implemented by an HDD (Hard Disk Drive), an SSD (Solid State Drive), an integrated circuit, or the like configured to store various kinds of information. The memory 7 may be implemented by a portable storage medium such as a CD (Compact Disc), a DVD (Digital Versatile Disc), or a flash memory other than the HDD and the SSD. Note that the memory 7 may be implemented by a drive device configured to read/write various kinds of information from/to a semiconductor memory element such as a flash memory or a RAM. In addition, the saving area of the memory 7 may exist in the medical information processing apparatus 1, or may exist in an external storage device connected via a network.

The memory 7 stores various kinds of conditions input via the input interface 3, information, programs corresponding to a plurality of functions executed by the processing circuitry 9, a machine learning model before learning, a model learning program, a radiation physics simulator executed by an acquisition function 93, and the like. The radiation physics simulator corresponds to, for example, a Monte Carlo simulator GATE (Geant4 Application for Tomographic Emission) that performs a Monte Carlo simulation for each single photon. Note that the radiation physics simulator is not limited to the GATE, and a program that executes another radiation physics simulation may be used.

The memory 7 stores a numerical phantom input to the radiation physics simulator. FIG. 2 is a view showing an example of the numerical phantom used for PET reconstruction learning. As shown in FIG. 2, the numerical phantom corresponds to for example, an RI concentration distribution without statistical noise. That is, the numerical phantom is a true ideal image and corresponds to ideal teaching data at the time of learning of a machine learning model. The numerical phantom is generated in advance for, for example, each imaging target, each RI concentration distribution, and each RI integration part. The imaging target is, for example, an organ, a body part or the like of an object to be captured by the medical image diagnosis apparatus.

Figure 13:
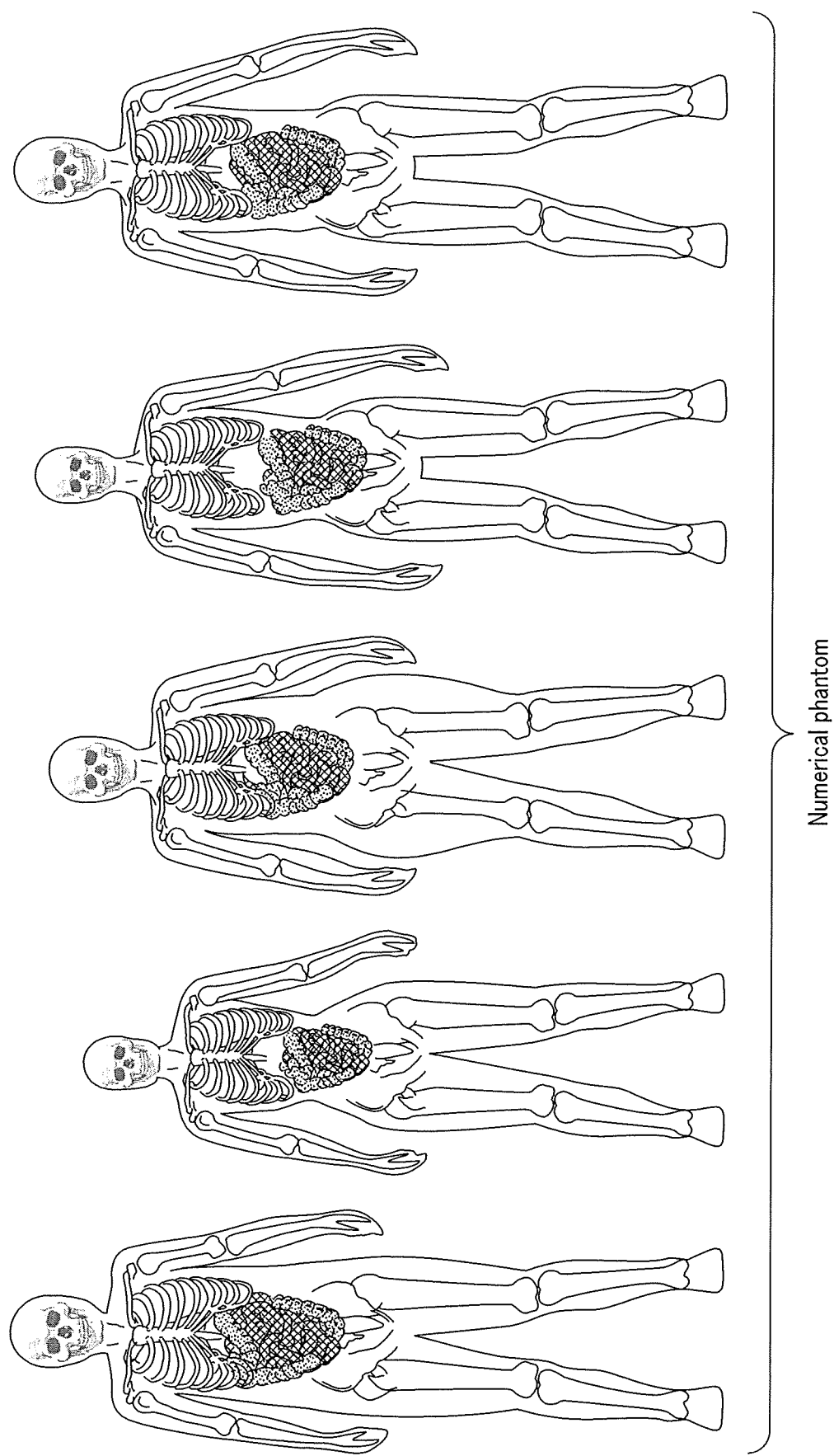
FIG. 13 is a view showing an example of a numerical phantom used in PET reconstruction learning, CT reconstruction learning, and the like in the first embodiment.

Note that the numerical phantom used to generate raw data concerning PET reconstruction learning and CT reconstruction learning is not limited to the numerical phantom shown in FIG. 2. As the numerical phantom used to generate raw data, a numerical phantom imitating an actual human body is preferably used. As the numerical phantom imitating an actual human body (an organ, a blood vessel, a bone, or the like), for example, an XCAT (eXtended CArdiac-Torso) phantom exists. The XCAT phantom is a digital numerical phantom modelled from a highly precise three-dimensional CT image by the non-uniform rational B-spline surfaces (NURBS) method. Note that the XCAT phantom may be a four-dimensional numerical phantom. The XCAT phantom can reproduce the respiration, heartbeat, or the like of a human body. FIG. 13 is a view showing an example of an XCAT phantom as a numerical phantom used to generate raw data. As shown in FIG. 13, the XCAT phantom imitates an actual human body. For example, when generating raw data, the XCAT phantom is used as the source of emission in the radiation physics simulator. At this time, the XCAT phantom corresponds to an ideal image.

Note that when a numerical phantom is used in CT reconstruction learning, the numerical phantom corresponds to the distribution of X-ray attenuation coefficients without various kinds of noise. At this time, the numerical phantom is generated in advance for each imaging target. The numerical phantom may be, for example, two-dimensional data corresponding to a predetermined section, or may be volume data.

The memory 7 may store raw data generated by the radiation physics simulator executed by the acquisition function 93. In addition, the memory 7 may store training data output by an output function 95. The training data is data that associates the numerical phantom and the raw data generated using the numerical phantom with the radiation physics simulator. In addition, the memory 7 may store an imaging condition and a detector condition associated with the generation of the raw data in the training data, which are attached to the training data. The memory 7 may also store a trained model learned by a model generation function 97. The trained model is a machine learning model to which a function is imparted to accept data acquired by imaging of an object and output a reconstructed image data concerning the data.

The processing circuitry 9 controls the operation of the entire medical information processing apparatus 1 in accordance with the electrical signal of an input operation output from the input interface 3. For example, the processing circuitry 9 includes, as hardware resources, a processor and storages such as a ROM and a RAM (none are shown). The processing circuitry 9 executes, by the processor that executes a program loaded into a program, an acceptance function 91, the acquisition function 93, the output function 95, the model generation function 97, and the like. Various kinds of functions performed by the acceptance function 91, the acquisition function 93, the output function 95, and the model generation function 97 are stored in the memory 7 in the form of a program executable by a computer. The processing circuitry 9 reads the programs corresponding to the various kinds of functions from the memory 7. The processing circuitry 9 is a processor that executes each read program, thereby implementing the function corresponding to the program.

In other words, the processing circuitry 9 that has read the programs has the plurality of functions in the processing circuitry 9 shown in FIG. 1. The processing circuitry 9 that implements the acceptance function 91, the acquisition function 93, the output function 95, and the model generation function 97 is an example of an acceptance unit, an acquisition unit, an output unit, and a model generation unit. The acceptance function 91, the acquisition function 93, the output function 95, and the model generation function 97 will be described concerning an operation according to this embodiment.

The word "processor" used in the above description means, for example, circuitry such as a CPU (Central Processing Unit), an MPU (Micro Processing Unit), a GPU (Graphical Processing Unit), an ASIC (Application Specific Integrated Circuit), or a programmable logic device (for example, an SPLD (Simple Programmable Logic Device), a CPLD (Complex Programmable Logic Device), or an FPGA (Field Programmable Gate Array)).

Note that instead of saving the programs in the memory 7, the programs may directly be incorporated in the circuitry of the processor. In this case, the processor reads and executes the programs incorporated in the circuitry, thereby implementing the various kinds of functions. Note that the plurality of functions are not always implemented by the single processing circuitry. The processing circuitry may be formed by combining a plurality of independent processors, and the processors in the processing circuitry may execute the programs, thereby implementing the plurality of functions. In other words, each of the above-described functions is configured as a program, and one processing circuitry may execute each program. In addition, a specific function may be implemented in dedicated independent program execution circuitry.

The overall arrangement of the medical information processing apparatus 1 according to this embodiment has schematically been explained above. An operation according to this embodiment will be described below. The operation according to this embodiment roughly includes processing (to be referred to as training data generation processing hereinafter) of generating training data and processing (to be referred to as trained model generation processing hereinafter) of generating a trained model.

Note that as a modification of this embodiment, in a case in which trained model generation processing is not executed, that is, in a case in which only training data generation processing is executed, the model generation function 97 in the processing circuitry 9 is unnecessary. In addition, as another modification of this embodiment, in a case in which training data generation processing is not executed, that is, in a case in which only trained model generation processing is executed, the acceptance function 91, the acquisition function 93, and the output function 95 in the processing circuitry 9 are unnecessary. At this time, the processing circuitry 9 executes trained model generation processing using training data generated by training data generation processing in another apparatus such as a cloud.

(Operation)

Figure 3:
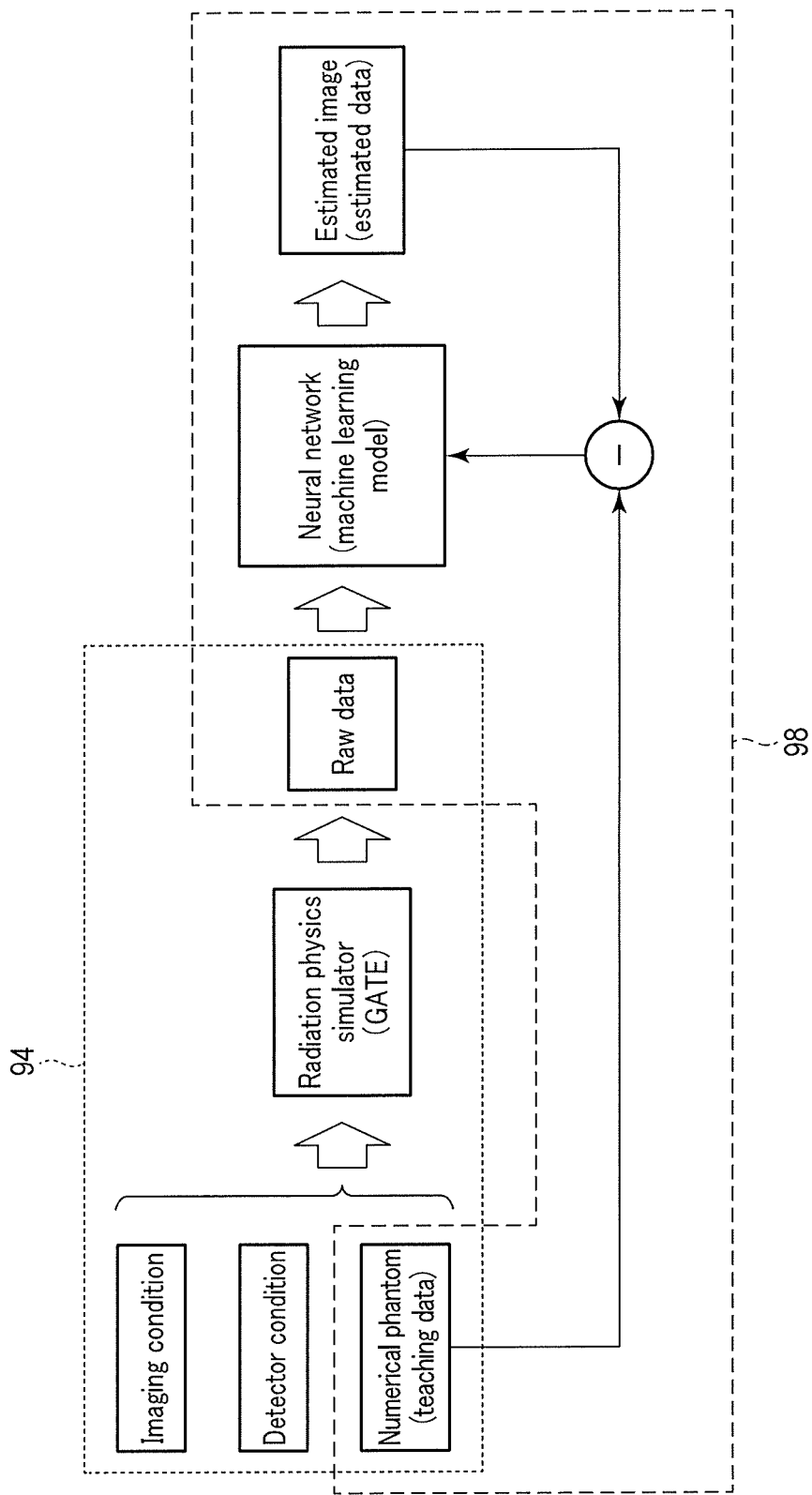
FIG. 3 is a view showing an example of the outline of training data generation processing and trained model generation processing in the first embodiment.

FIG. 3 is a view showing an example of the outline of training data generation processing 94 and trained model generation processing 98. In the training data generation processing 94 shown in FIG. 3, an imaging condition, a detector condition, and a numerical phantom are input to the radiation physics simulator (GATE). The radiation physics simulator (GATE) sequentially tracks the behavior (for example, attenuation, scattering, and the like) of gamma rays in the numerical phantom and in the scintillation crystal of the detector using the input imaging condition, detector condition, and numerical phantom, thereby generating raw data (to be referred to as list mode data hereinafter) corresponding to a list mode. Note that the raw data is not limited to list mode data, and may be raw data in a histogram mode, raw data in a two-dimensional acquisition mode, raw data in a three-dimensional acquisition mode, a sinogram, or the like. For example, statistical noise, the influence of attenuation and scattering of gamma rays, X-rays, or the like, and information (information of actual apparatus) concerning the geometrical arrangement are mixed in the raw data.

Note that in the training data generation processing 94, if a plurality of numerical phantoms along the time series are used as shown in FIG. 4, the plurality of numerical phantoms along the time series may be input to the radiation physics simulator (GATE). At this time, the radiation physics simulator (GATE) generates raw data (list mode data) in the list mode. The list mode data corresponding to the plurality of numerical phantoms along the time series is used in, for example, PET imaging (PET scan) using an RI having a short half-life such as rubidium 82 ($^{82}$Rb) as training data used to generate a trained model that outputs a reconstructed image concerning, for example, evaluation of a myocardial blood flow.

More specifically, in the training data generation processing 94, the imaging condition and the detector condition are set as fixed values, and each of the plurality of numerical phantoms is input to the radiation physics simulator together with the imaging condition and the detector condition. By these inputs to the radiation physics simulator, the radiation physics simulator generates raw data corresponding to each of the plurality of numerical phantoms. Next, raw data corresponding to a numerical phantom and the numerical phantom are associated via the radiation physics simulator. Training data is generated by this association. N training data corresponding to the combination of the imaging condition and the detector condition and including different numerical phantoms will be referred to as a training data set hereinafter. N is a sufficiently large natural number that generates only an error equal to or less than a threshold, and is set in advance by the operator via the input interface 3 or the like. In addition, N and the threshold are stored in the memory 7. The error will be described later.

Figure 5:
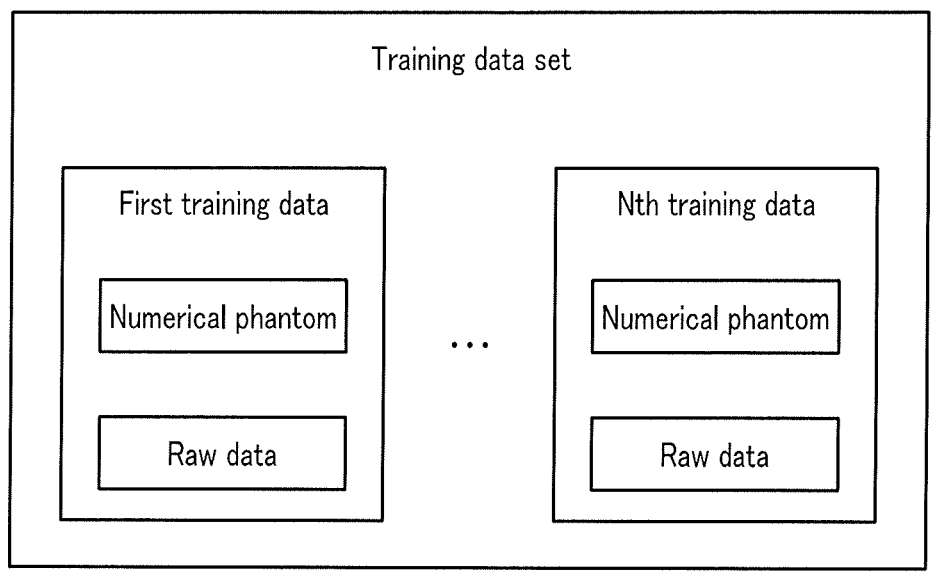
FIG. 5 is a view showing an example of a training data set in the first embodiment.

FIG. 5 is a view showing an example of a training data set. With the above-described processing, training data sets as many as the number of combinations of imaging conditions and detector conditions are generated by the training data generation processing 94. Next, in the trained model generation processing 98, a neural network is learned using training data included in a training data set corresponding to a combination of an imaging condition and a detector condition. By this learning, a trained model corresponding to the combination of the imaging condition and the detector condition is generated. At this time, the total number of trained models is the product of the number of elements included in the imaging condition and the number of elements included in the detector condition.

Figure 6:
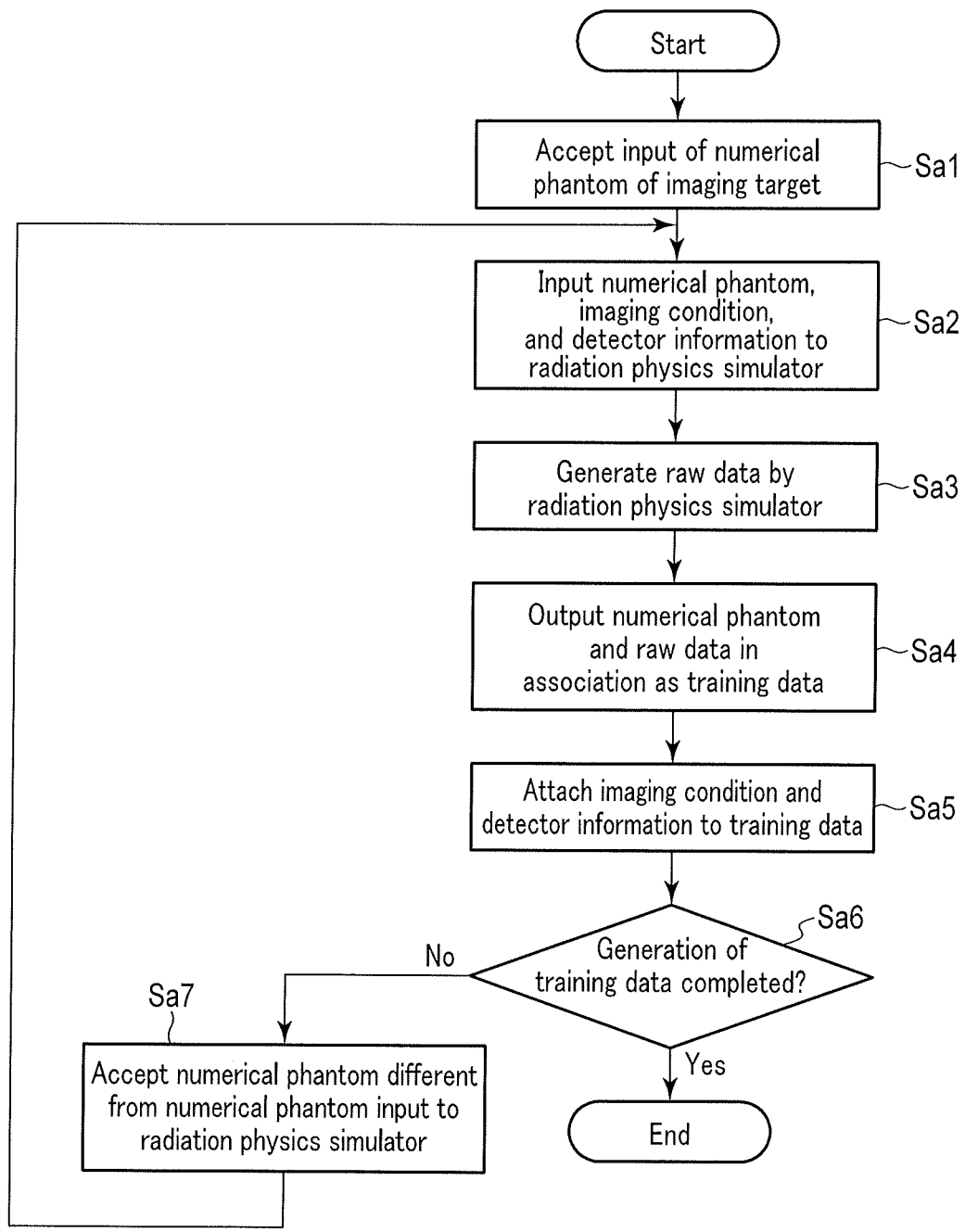
FIG. 6 is a flowchart showing an example of a training data generation procedure in the first embodiment.

The procedure of the training data generation processing 94 will be described below. FIG. 6 is a flowchart showing an example of a training data generation procedure executed by the processing circuitry 9.

(Training Data Generation Processing)

In the stage prior to step Sa1, the input interface 3 inputs an imaging condition and a detector condition based on an instruction of the operator.

(Step Sa1)

The processing circuitry 9 accepts the input of a numerical phantom of an imaging target by the acceptance function 91. For example, the processing circuitry 9 accepts, from the memory 7 or from an external storage device via a network, a numerical phantom to be input to the radiation physics simulator, more specifically, an image corresponding to the numerical phantom.

Note that the processing circuitry 9 may automatically generate a numerical phantom. For example, the processing circuitry 9 generates a numerical phantom according to an imaging target, an RI concentration distribution, and an RI integration part based on examination contents, a disease name, a fault occurrence point in the disease, and the like.

(Step Sa2)

The processing circuitry 9 inputs the numerical phantom, the imaging condition, and the detector condition to the radiation physics simulator by the acceptance function 91.

(Step Sa3)

Raw data is generated by the radiation physics simulator. The processing circuitry 9 acquires raw data based on an image corresponding to the numerical phantom and a predetermined imaging condition (scan condition) by the acquisition function 93. The raw data is acquired by, for example, the radiation physics simulator. More specifically, the processing circuitry 9 executes the radiation physics simulator to which the numerical phantom, the imaging condition, and the detector condition are input. The processing circuitry 9 acquires, as raw data, data output from the radiation physics simulator. The raw data is formed by, for example, a detection event of gamma rays corresponding to an arbitrary actual acquisition time.

(Step Sa4)

By the output function 95, the processing circuitry 9 associates the numerical phantom and the raw data with each other, and outputs them as training data. More specifically, the processing circuitry 9 associates the numerical phantom input to the radiation physics simulator with the raw data output from the radiation physics simulator, thereby generating training data. That is, as training data used to generate a trained model that accepts data acquired by scan for the object and outputs a reconstructed image data corresponding to the data, the processing circuitry 9 associates the image corresponding to the numerical phantom with the raw data and outputs them. The processing circuitry 9 outputs the training data to the memory of its own.

(Step Sa5)

The processing circuitry 9 attaches the imaging condition and the detector condition to the training data by the output function 95. More specifically, the processing circuitry 9 attaches the imaging condition and the detector condition, which are input to the radiation physics simulator in step Sa2, to the training data generated in step Sa4.

(Step Sa6)

If the generation of the training data is completed (YES in step Sa6), the training data generation processing 94 ends. At this time, the processing circuitry 9 brings N training data together by the output function 95, thereby generating training data set. The processing circuitry 9 outputs the training data set to the memory 7 or the external storage device via the network.

If the generation of the training data is not completed (NO in step Sa6), the process of step Sa7 is executed. Determining the presence/absence of completion of the training data generation processing 94 in this step corresponds to, for example, determining whether N training data are generated.

(Step Sa7)

The processing circuitry 9 accepts a numerical phantom different from the numerical phantom input to the radiation physics simulator in step Sa2. Note that the numerical phantom accepted in this step may automatically be generated as in step Sa1. After step Sa7, the processes of steps Sa2 to Sa6 are repeated until N training data are generated.

The imaging condition and the detector condition are updated, and the processes of steps Sa1 to Sa7 are repeated. By repeating the processes, the processing circuitry 9 generates a plurality of training data sets according to the combinations of imaging conditions and detector conditions.

The above-described processing procedure of the training data generation processing 94 is merely an example, and, for example, the following processing procedure may be used. First, by the acquisition function 93, the processing circuitry 9 changes the imaging condition and the detector condition at random, and sequentially inputs a plurality of numerical phantoms to the radiation physics simulator. By the sequential input, the processing circuitry 9 generates raw data corresponding to each of the plurality of numerical phantoms. Next, by the output function 95, the processing circuitry 9 outputs, as training data, a combination of raw data and a numerical phantom belonging to the same imaging condition and the same detector condition. Subsequently, the processing circuitry 9 brings training data belonging to the same imaging condition and the same detector condition together. By bringing the training data together, the processing circuitry 9 generates a plurality of training data sets corresponding to the combinations of imaging conditions and detector conditions. Finally, the processing circuitry 9 attaches the corresponding imaging conditions and detector conditions to the training data sets.

The trained model generation processing 98 will be described below. In the trained model generation processing 98 shown in FIG. 3, raw data is input to the input layer of the neural network that is a machine learning model before learning. By the model generation function 97, the processing circuitry 9 propagates the raw data forward from the input layer to the output layer of the neural network via at least one intermediate layer. By the forward propagation, the processing circuitry 9 outputs an estimated image. The processing circuitry 9 calculates a parameter (weight) in the neural network in accordance with backpropagation using the difference between the estimated image and the numerical phantom, that is, the error between the teaching data and the estimated data. The processing circuitry 9 repeats the training data generation processing 94 and the trained model generation processing 98 until the error becomes equal to or less than a predetermined threshold. By the repeat, the processing circuitry 9 generates a trained model.

Preferably, the processing shown in FIG. 3 is repeated for each combination of an imaging condition and a detector condition. By the repeat of the processing, a trained model corresponding to these conditions is generated. That is, a plurality of trained models corresponding to the combinations of imaging conditions and detector conditions are generated. Note that the processing shown in FIG. 3 may be repeated while changing the value of a hyperparameter in addition to the combination of the imaging condition and the detector condition. At this time, a trained model corresponding to the combination of the imaging condition and the detector condition and the hyperparameter is generated.

Figure 7:
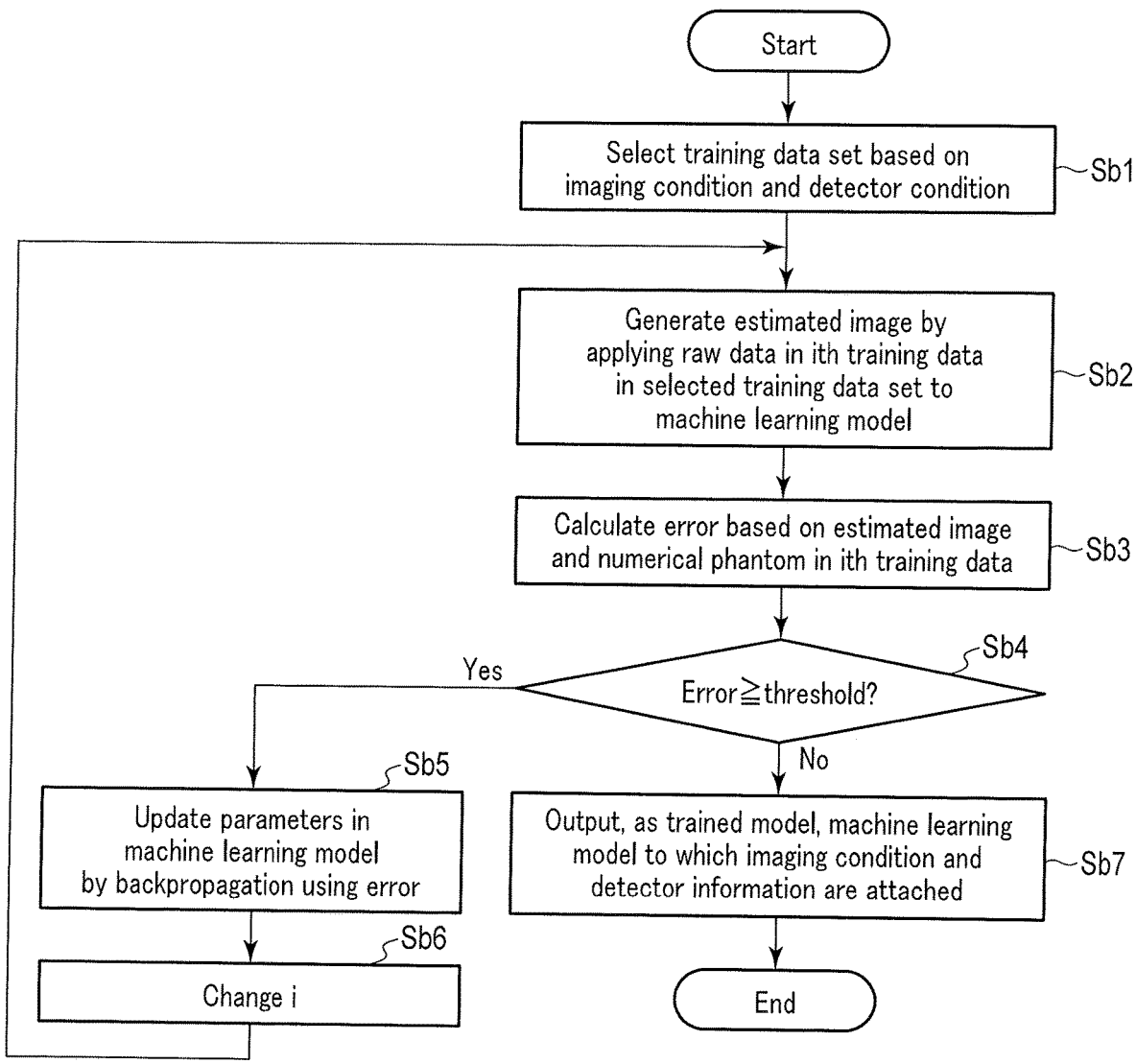
FIG. 7 is a flowchart showing an example of a trained model generation procedure in the first embodiment.

The procedure of the trained model generation processing 98 will be described below. FIG. 7 is a flowchart showing an example of a trained model generation procedure executed by the model generation function 97 of the processing circuitry 9. The processing procedure shown in FIG. 7 is executed by the processing circuitry 9 based on, for example, a model learning program. The trained model generation procedure shown in FIG. 7 represents sequential learning. Note that the training method is not limited to sequential learning, and an arbitrary training method such as batch learning or mini batch learning can be applied to the model generation function 97.

(Trained Model Generation Processing)

In the stage prior to step Sb1, the input interface 3 inputs an imaging condition and a detector condition based on an instruction of the operator. Note that the input interface 3 may input a hyperparameter selection instruction. At this time, a trained model generated by the trained model generation processing 98 is associated with the quality of a reconstructed image, and, for example, associated with the application purpose of the reconstructed image generated by the trained model such as diagnosis or imaging confirmation.

(Step Sb1).

By the model generation function 97, the processing circuitry 9 selects a training data set based on the input imaging condition and detector condition (to be referred to as input conditions hereinafter). More specifically, the processing circuitry 9 selects a training data set corresponding to the input conditions from a plurality of training data sets corresponding to the combinations of imaging conditions and detector conditions. The processing circuitry 9 sets a natural number that discriminates training data in the selected training data set to an initial value. The initial value can be any natural number from 1 to N. Assume that the initial value is i that satisfies 1≤i≤N to simplify the description.

(Step Sb2)

Figure 8:
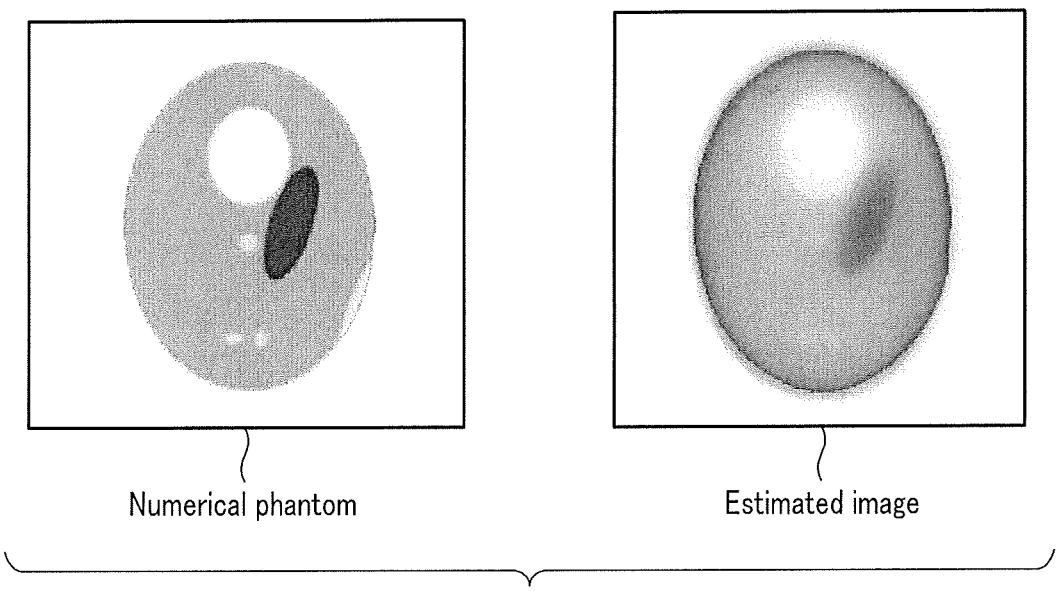
FIG. 8 is a view showing an example of a numerical phantom and an estimated image used in generation of a trained model in the first embodiment.

By the model generation function 97, the processing circuitry 9 applies raw data in the ith training data of the selected training data set to the machine learning model. The processing circuitry 9 thus generates an estimated image. FIG. 8 is a view showing an example of a numerical phantom and an estimated image. As shown in FIG. 8, the quality of the estimated image is lower than that of the numerical phantom.

(Step Sb3)

Based on the numerical phantom and the estimated image in the ith training data, the processing circuitry 9 calculates the error between the two images by the model generation function 97. More specifically, the processing circuitry 9 generates the difference image between the numerical phantom and the estimated image shown in FIG. 8. Next, the processing circuitry 9 calculates, as the error, the square-sum of a plurality of pixel values in the difference image. Note that the error is not limited to the square-sum, and an arbitrary statistical value, for example, a mean square error may be used as the error.

(Step Sb4)

The processing circuitry 9 compares the error and a threshold by the model generation function 97. If the error is equal to or more than the threshold (YES in step Sb4), the process of step Sb5 is executed. If the error is less than the threshold (NO in step Sb4), the process of step Sb7 is executed.

(Step Sb5)

By the model generation function 97, the processing circuitry 9 updates the parameters in the machine learning model by backpropagation using the error. More specifically, in the sequential learning, the processing circuitry 9 updates the parameters in the machine learning model by a stochastic gradient descent method using the error.

(Step Sb6)

By the model generation function 97, the processing circuitry 9 changes the natural number i that discriminates the training data in the selected training data set. Next, the processing circuitry 9 repeats the processes of steps Sb2 to Sb4.

(Step Sb7)

By the model generation function 97, the processing circuitry 9 outputs, as a trained model, the machine learning model to which the imaging condition and the detector condition are attached. More specifically, the processing circuitry 9 attaches the imaging condition and the detector condition, which are used at the time of learning of the machine learning model, to the machine learning model used in step Sb2. The processing circuitry 9 outputs the machine learning model to which these conditions are attached to the memory 7 or the external storage device as a trained model. Note that if the processes of steps Sb1 to Sb7 are executed in accordance with a hyperparameter in addition to the combination of the imaging condition and the detector condition, the processing circuitry 9 attaches, to the trained model, an application purpose corresponding to the hyperparameter used to generate the trained model.

According to the above-described arrangement and operation, the following effects can be obtained.

According to the medical information processing apparatus 1 of this embodiment, it is possible to accept an input of an image corresponding to a numerical phantom, acquire raw data generated based on an image corresponding to the numerical phantom and a predetermined imaging condition (scan condition), and output the image corresponding to the numerical phantom and the raw data in association with each other as training data used to generate a trained model to which a function is imparted to accept data acquired by scan of the object and output a reconstructed image data concerning the data. Hence, according to the medical information processing apparatus 1, it is possible to, when acquiring training data, generate raw data for learning by a radiation physics simulator using a numerical phantom such as an XCAT that is strictly accurate as an ideal image and generate training data used for learning of a machine learning model by the generated raw data and the numerical phantom without acquiring an ideal image serving as teaching data by actual PET imaging.

That is, according to the medical information processing apparatus 1 of this embodiment, it is unnecessary to administer an enormous amount of radiopharmaceutical to an object (patient) and increase the count of photons in raw data as much as possible, or increase the count as much as possible by long time acquisition using a normal administration amount of radiopharmaceutical. In other words, according to the medical information processing apparatus 1, since generation of training data is not limited by data acquisition for a finite time, the efficiency of generation of training data can be improved. Additionally, according to the medical information processing apparatus 1, the burden on the object by exposure for generation of training data can be eliminated, and training data can be generated using an ideal image (numerical phantom) in a true sense as teaching data.

In addition, according to the medical information processing apparatus 1 of this embodiment, it is possible to learn a machine learning model using the generated training data. Additionally, according to the medical information processing apparatus 1 of this embodiment, it is possible to generate raw data further using detector conditions concerning a plurality of detectors concerning acquisition of data.

In addition, according to the medical information processing apparatus 1, concerning a detector condition including at least one of the radiation detection characteristic of each of a plurality of detectors, the gap between adjacent detectors in the plurality of detectors, and the geometrical arrangement of the plurality of detectors, and an imaging condition including at least one of the count of gamma rays concerning data, the count rate of gamma rays, and a nuclide name concerning generation of gamma rays, or at least one of a scan method concerning acquisition of data, the number of views used for reconstruction, a tube voltage, and a tube current, the detector condition and the imaging condition input to the radiation physics simulator can be attached to the training data.

Furthermore, according to the medical information processing apparatus 1, it is possible to generate a trained model by learning a machine learning model using training data. More specifically, according to the medical information processing apparatus 1, the machine learning model is learned using training data corresponding to the combination of an imaging condition and a detector condition, thereby generating a trained model corresponding to the combination of the imaging condition and the detector condition. In addition, according to the medical information processing apparatus 1, a hyperparameter in the machine learning model before learning is selected, thereby generating a trained model in accordance with the quality of a reconstructed image, that is, the application purpose of the reconstructed image.

As described above, according to the medical information processing apparatus 1, it is possible to generate a trained model according to the combination of an imaging condition and a detector condition or the application purpose of a reconstructed image. That is, according to the medical information processing apparatus 1, it is possible to generate a trained model incorporating various kinds of corrections (for example, correction (normalization) concerning the geometrical arrangement of a plurality of detectors and a detector gap, correction concerning a count loss, a time-rate change of the count rate in the acquisition time when using a short-lived nuclide, and the like) concerning generation of a reconstructed image data. For this reason, since the trained model generated by the medical information processing apparatus 1 obtains a function of correcting the influence of the geometrical arrangement, the gamma ray detection efficiency, and the detector gap, for example, the problem of over-fitting for a specific count can also be solved.

In addition, according to the medical information processing apparatus 1, raw data of a wider detection count is generated by the radiation physics simulator, and learning is executed using the raw data and a numerical phantom. This can avoid over-fitting caused by the difference of the imaging condition and the detector condition, and can improve generalization performance according to the imaging condition and the detector condition in the trained model.

Second Embodiment

A first application example and a second application example will be described below using a PET apparatus and an X-ray CT apparatus as examples of a medical image diagnosis apparatus including a medical information processing apparatus according to this embodiment. The medical information processing apparatus according to this embodiment includes a storage unit configured to store a trained model to which a function is imparted to directly output a reconstructed image data concerning data based on the data acquired by imaging for an object, and which is learned using raw data generated by a radiation physics simulator using a numerical phantom and the numerical phantom, a data acquisition unit configured to receive acquired data, and a reconstruction unit configured to generate a reconstructed image data by inputting the acquired data to the trained model. That is, the medical information processing apparatus includes processing circuitry. The processing circuitry is configured to receive data acquired by scan of an object, and output a reconstructed image data based on the data and a trained model that accepts the data as input data and outputs a reconstructed image data corresponding to the data. The trained model is trained by learning using raw data generated based on a numerical phantom and the numerical phantom. More specifically, the memory (storage unit) of the medical information processing apparatus included in the medical image diagnosis apparatus stores, of a plurality of trained models generated by the first embodiment, at least one trained model that matches the detector condition in the medical image diagnosis apparatus.

First Application Example

The overall arrangement of a PET apparatus 100 according to this application example will be described with reference to FIG. 9. FIG. 9 is a view showing an example of the arrangement of the PET apparatus 100. As shown in FIG. 9, the PET apparatus 100 includes a PET gantry (data acquisition unit) 10, a couch 50, and a console 70. The medical information processing apparatus according to this application example includes a plurality of constituent elements in the console 70. Note that the medical information processing apparatus according to this application example may include the PET gantry 10. Note that FIG. 9 shows a plurality of PET gantries 10 for the descriptive convenience. Typically, the PET gantry 10 and the couch 50 are installed in a common examination room. In addition, the console 70 is installed in a control room next to the examination room. The PET gantry 10 is an imaging apparatus that executes PET imaging (PET scan) for an object P. The couch 50 movably supports a couch top 53 on which the object P of the imaging target is placed. The console 70 includes a computer configured to control the PET gantry 10 and the couch 50.

The geometrical arrangement of a plurality of detectors in the PET apparatus 100 is a ring-shaped arrangement, as shown in FIG. 9. In this case, a memory 74 stores at least one trained model to which a detector condition including the ring-shaped geometrical arrangement is attached. To make a detailed description, the memory 74 is assumed to store a trained model (to be referred to as a high count model hereinafter) to which an imaging condition including a high count is attached, and a trained model (to be referred to as a low count model hereinafter) to which an imaging condition including a low count is attached. Note that the memory 74 may store a trained model to which an imaging condition including an RI name used for PET imaging is attached, for example, a trained model (to be referred to as a short half-life model hereinafter) corresponding to rubidium 82 ($^{82}$Rb). In these cases, for example, the high count model corresponds to the examination name of PET imaging executed by a high count, the low count model corresponds to the examination name of PET imaging executed by a low count, and the short half-life model corresponds to the examination name or examination contents of PET imaging using an RI of a short half-life.

Note that the memory 74 may store a low count model, a high count model, and a short half-life model for each application purpose of a PET image reconstructed by a trained model. For example, if a PET image has two types of application purposes including diagnosis and imaging confirmation, the memory 74 stores two types for each of the low count model, the high count model, and the short half-life model, that is, six patterns of trained models.

As shown in FIG. 9, the PET gantry 10 includes a detector ring 11, signal processing circuitry 13, and coincidence circuitry 15.

The detector ring 11 includes a plurality of gamma ray detectors 17 arranged on the circumference about a center axis Z. Note that the arrangement of the plurality of gamma ray detectors 17 is not limited to the ring shape shown in FIG. 9, and may be, for example, an elliptical shape, a triangular shape, or the like. At this time, the memory 74 stores a trained model corresponding to the arrangement shape of the plurality of gamma ray detectors 17. A field of view (FOV) is set on the opening portion of the detector ring 11. The object P is positioned such that the imaging part of the object P is included in the field of view. A pharmaceutical labeled by a positron-emitting radionuclide is administered to the object P. Positrons emitted from the positron-emitting radionuclide cause pair annihilation with electrons on the periphery. By the pair annihilation, a pair of pair annihilation gamma rays is generated.

The gamma ray detectors 17 detect the pair annihilation gamma rays discharged from the body of the object P. The gamma ray detectors 17 each generates an electrical signal corresponding to the light amount of the detected pair annihilation gamma rays. For example, the gamma ray detector 17 includes a plurality of scintillators and a plurality of photomultipliers. The scintillator receives the pair annihilation gamma rays derived from the radioisotope in the object P and generates light. The photomultiplier generates an electrical signal corresponding to the amount of light. The generated electrical signal is supplied to the signal processing circuitry 13. Note that the gamma ray detector 17 may be an SiPM detector or a semiconductor detector.

The signal processing circuitry 13 generates single event data based on the electrical signals output from the gamma ray detectors 17. More specifically, the signal processing circuitry 13 performs detection time measurement processing, position calculation processing, and energy calculation processing for the electrical signal. The signal processing circuitry 13 is implemented by an ASIC, FPGA, CPLD, SPLD, or the like configured to be able to execute detection time measurement processing, position calculation processing, and energy calculation processing.

The signal processing circuitry 13 measures the detection time of gamma rays in the gamma ray detector 17 by the detection time measurement processing. More specifically, the signal processing circuitry 13 monitors the peak value of the electrical signal output from the gamma ray detector 17. The signal processing circuitry 13 measures, as the detection time, a time at which the peak value exceeds a threshold set in advance. In other words, the signal processing circuitry 13 detects that the peak value exceeds the threshold, thereby electrically detecting annihilation gamma rays.

The signal processing circuitry 13 calculates the incident position of the pair annihilation gamma rays based on the electrical signal output from the gamma ray detector 17 by the position calculation processing. The incident position of the annihilation gamma rays corresponds to the position coordinates of the scintillator in which the annihilation gamma rays enter.

The signal processing circuitry 13 calculates the energy value of the detected pair annihilation gamma rays based on the electrical signals output from the gamma ray detectors 17 by the energy calculation processing. The signal processing circuitry 13 associates the data of the detection time, the data of the position coordinates, and the data of the energy value concerning the single event. The combination of the data of the energy value, the data of the position coordinates, and the data of the detection time concerning the single event is called single event data. The single event data is generated successively every time annihilation gamma rays are detected. The generated single event data is supplied to the coincidence circuitry 15.

The coincidence circuitry 15 performs coincidence processing for the single event data from the signal processing circuitry 13. As hardware resource, the coincidence circuitry 15 is implemented by an ASIC, FPGA, CPLD, SPLD, or the like configured to be able to execute coincidence processing. By the coincidence processing, the coincidence circuitry 15 repetitively specifies single event data concerning two single events (a pair of single events) within a predetermined time slot from repetitively supplied single event data. The pair of single events is estimated as derived from pair annihilation gamma rays generated from the same pair annihilation point. The pair of single events will be referred to as a coincidence event. A line that connects a pair of gamma ray detectors 17 (more specifically, scintillators) that have detected the pair annihilation gamma rays will be referred to as an LOR (Line Of Response). Event data concerning the pair of single events that forms the LOR will be referred to as coincidence event data. The coincidence event data and the single event data are transmitted to the console 70. Note that if the coincidence event data and the single event data are not particularly discriminated, these will be referred tows PET event data together.

Note that in the above-described arrangement, the signal processing circuitry 13 and the coincidence circuitry 15 are included in the PET gantry 10. However, the application example is not limited to this. For example, the coincidence circuitry 15 or both of the signal processing circuitry 13 and the coincidence circuitry 15 may be included in an apparatus different from the PET gantry 10. In addition, one coincidence circuitry 15 may be provided for a plurality of signal processing circuitry 13 included in the PET gantry 10. Alternatively, a plurality of signal processing circuitry 13 included in the PET gantry 10 may be divided into a plurality of groups, and one coincidence circuitry 15 may be provided for each group.

As shown in FIG. 9, the object P of the scan target is placed on the couch 50. The couch 50 moves the placed object P. The couch 50 includes a base 51, a support frame 52, the couch top 53, and a couch driving device 54. The base 51 is installed on a floor surface. The base 51 is a housing that supports the support frame 52 so as to move it in a vertical direction (Y-axis direction) with respect to the floor surface. The support frame 52 is a frame provided on the base 51. The support frame 52 supports the couch top 53 so as to slide it along the center axis Z. The couch top 53 is a plate on which the object P is placed.

The couch driving device 54 is stored in the housing of the couch 50. The couch driving device 54 is a motor or an actuator configured to generate a power to move the couch top 53 on which the object P is placed and the support frame 52. The couch driving device 54 operates under the control of the console 70 or the like.

As shown in FIG. 9, the console 70 includes a PET data memory 71, an input interface (input unit) 72, a display (display unit) 73, the memory (storage unit) 74, and processing circuitry (processing unit) 75. Data communication between the PET data memory 71, the input interface 72, the display 73, the memory 74, and the processing circuitry 75 is performed, for example, via a wired bus or wirelessly.

The PET data memory 71 is a storage device that stores single event data and coincidence event data transmitted from the PET gantry 10. The PET data memory 71 is a storage device implemented by an HDD, an SSD, an integrated circuit, or the like. The event data stored in the PET data memory 71 may be any data format such as list mode data or histogram data. These data stored in the PET data memory 71 will generically be referred to as acquired data hereinafter.

The input interface (input unit) 72 accepts various kinds of input operations from the operator. The input interface 72 converts an accepted input operation into an electrical signal. The input interface 72 outputs the converted electrical signal to the processing circuitry 75. The input interface 72 supplies an output signal from an input device to the processing circuitry 75 via the bus. More specifically, the input interface 72 inputs examination contents such as an examination name, an imaging condition, and the like in accordance with an instruction of the operator before execution of PET imaging for the object P. Note that the examination contents may be order information of an examination input from a radiology information system (to be referred to as an RIS hereinafter) via a network. At this time, the processing circuitry 75 extracts the examination contents from the order information. In addition, the input interface 72 may input the application purpose or quality of a PET image based on an instruction of the operator. Note that an input device serving as an implementation means of the input interface 72 is similar to that in the first embodiment, and a description thereof will be omitted.

The display 73 displays various kinds of information under the control of a display control function 754 of the processing circuitry 75. The display 73 displays, for example, a GUI concerning input of examination contents, an imaging condition, and the like. The display 73 displays a PET image generated by a reconstruction function 751 of the processing circuitry 75 and a medical image generated by an image processing function 752. Note that the display 73 may display, for example, a GUI concerning input of image quality, an application purpose, or the like. A display device serving as an implementation means of the display 73 is similar to that in the first embodiment, and a description thereof will be omitted.

The memory 74 stores various kinds of conditions input via the input interface 72, information, programs corresponding to a plurality of functions executed by the processing circuitry 75, a PET image generated by the reconstruction function 751, and a medical image generated by the image processing function 752. The memory 74 stores a trained model corresponding to the geometrical arrangement of the plurality of detectors (gamma ray detectors 17) concerning acquisition of data. That is, the memory 74 stores at least one trained model corresponding to a detector condition concerning the geometrical arrangement of the gamma ray detectors 17. The memory 74 stores a plurality of trained models in accordance with an imaging condition (scan condition) including at least one of the count of gamma rays concerning data, the count rate of gamma rays, and a nuclide name concerning generation of gamma rays. Note that the memory 74 may store a plurality of trained models in accordance with the application purpose of a reconstructed image (PET image). The trained model incorporates correction concerning generation of a reconstructed image (PET image) in learning by raw data and a numerical phantom. For example, as described above, the memory 74 stores a high count model a low count model and a short half-life model together with an associated imaging condition and also together with an application purpose in some cases. In addition, a storage device serving as an implementation means of the memory 74 is similar to that in the first embodiment, and a description thereof will be omitted.

The processing circuitry 75 includes, as hardware resources, a processor such as a CPU, an MPU, or a GPU and memories such as a ROM and a RAM. The processing circuitry 75 executes various kinds of programs read from the memory, thereby implementing the reconstruction function 751, the image processing function 752, an imaging control function 753, and the display control function 754. Note that the reconstruction function 751, the image processing function 752, the imaging control function 753, and the display control function 754 may be implemented by processing circuitry of one board, or may be implemented distributively by processing circuitry of a plurality of boards. The processing circuitry 75 that implements the reconstruction function 751, the image processing function 752, the imaging control function 753, and the display control function 754 is an example of a reconstruction unit, an image processing unit, an imaging control unit, and a display control unit.

By the reconstruction function 751, the processing circuitry 75 selects a trained model stored in the memory 74 in accordance with an imaging condition and an application purpose input via the input interface 72. Note that the processing circuitry 75 in the medical information processing apparatus acquires data from the PET gantry 10 (more specifically, the coincidence circuitry 15) or the PET data memory 71. The processing circuitry 75 inputs the data to the selected trained model. The processing circuitry 75 executes the trained model to which the acquired data is input. The processing circuitry 75 executes the trained model, thereby generating a PET image as a reconstructed image data of the acquired data. The processing circuitry 75 outputs the generated PET image to the memory 74 and the display 73.

By the image processing function 752, the processing circuitry 75 performs various kinds of image processing for the PET image reconstructed by the reconstruction function 751. For example, the processing circuitry 75 executes three-dimensional image processing such as volume rendering, surface volume rendering, pixel value projection processing, MPR (Multi-Planer Reconstruction) processing, and CPR (Curved MPR) processing for the PET image. The processing circuitry 75 thus generates a medical image.

By the imaging control function 753, the processing circuitry 75 synchronously controls the PET gantry 10 and the couch 50 to perform PET imaging. In addition, the processing circuitry 75 may execute positioning scan by the PET gantry 10. For the PET positioning scan, the processing circuitry 75 synchronously controls the PET gantry 10 and the couch 50. The processing circuitry 75 sets an acquisition area concerning PET imaging.

The processing circuitry 75 displays various kinds of information on the display 73 by the display control function 754. For example, the processing circuitry 75 displays a PET image reconstructed by the reconstruction function 751 on the display 73. In addition, the processing circuitry 75 displays a GUI for various kinds of settings and inputs on the display 73.

Figure 10:
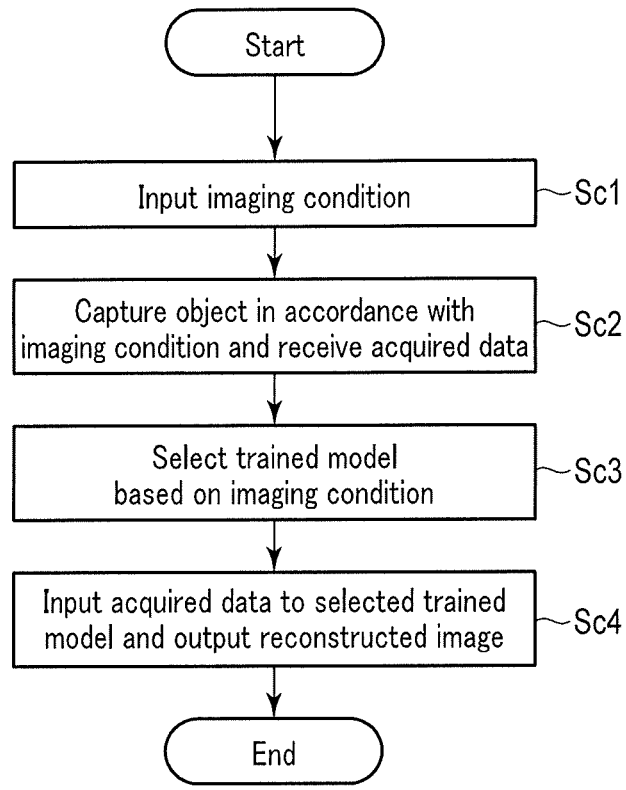
FIG. 10 is a flowchart showing an example of the procedure of PET reconstruction processing in the first application example of the second embodiment.

The overall arrangement of the PET apparatus 100 according to this application example has been described above. The processing procedure (to be referred to as PET reconstruction processing hereinafter) of reconstruction of a PET image in the PET apparatus 100 will be described below. FIG. 10 is a flowchart showing an example of the procedure of PET reconstruction processing executed by the processing circuitry 75.

(PET Reconstruction Processing)

(Step Sc1)

The input interface 72 inputs an imaging condition concerning a PET image before execution of PET imaging (PET scan). At this time, the input interface 72 may input the application purpose of the PET image. Note that the processing circuitry 75 may extract examination contents from the order information of the examination input from the RIS.

(Step Sc2)

The processing circuitry 75 captures the object P in accordance with the imaging condition by the imaging control function 753, and receives acquired data. The PET data memory 71 stores the acquired data.

(Step Sc3)

By the reconstruction function 751, the processing circuitry 75 selects a trained model to be used to reconstruct a PET image, based on the imaging condition, from a plurality of trained models stored in the memory 74. For example, if a low count is included in the imaging condition, that is, if the acquisition time is short, the processing circuitry 75 selects a low count model. If a high count is included in the imaging condition, that is, if the acquisition time is long, the processing circuitry 75 selects a high count model. If a nuclide of a short half-life such as rubidium 82 ($^{82}$Rb) is included in the imaging condition, the processing circuitry 75 selects a short half-life model. Note that the processing circuitry 75 may select the trained model to be used to reconstruct a PET image based on the examination contents. In addition, the processing circuitry 75 may select the trained model to be used to reconstruct a PET image based on at least one of the imaging condition and the application purpose of the PET image. That is, the processing circuitry 75 may receive a selection of a trained model corresponding to the application purpose from the plurality of trained models stored in the memory 74.

(Step Sc4)

Figure 11:
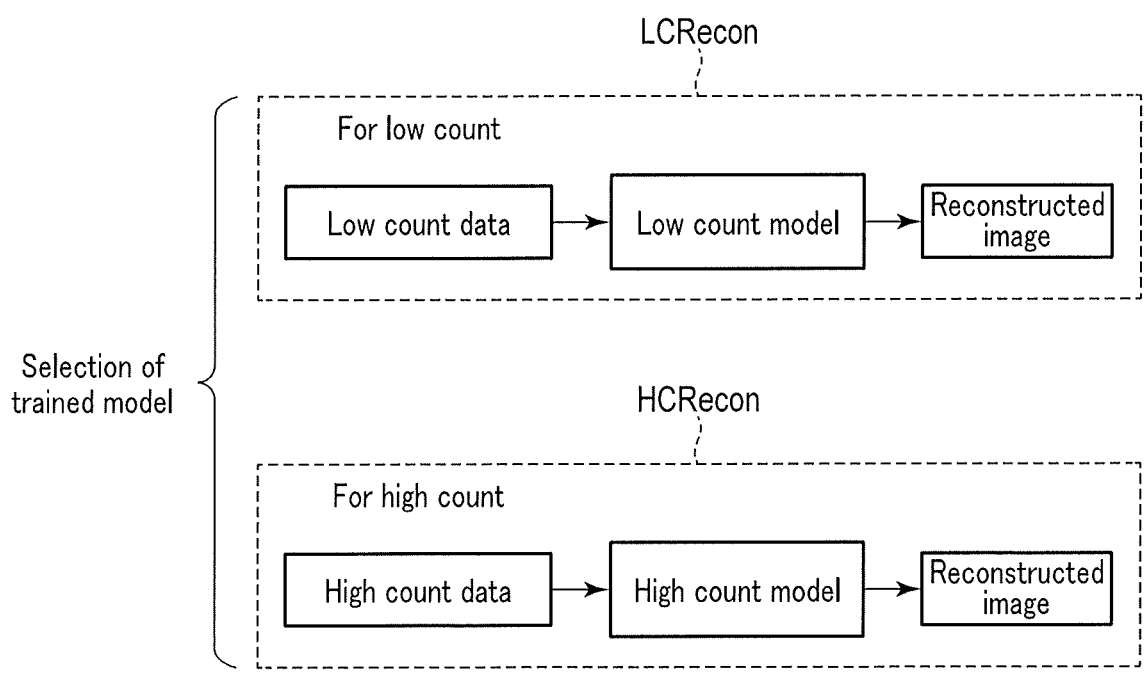
FIG. 11 is a view showing an example of reconstruction processing in a case in which a selected trained model is a low count model and reconstruction processing in a case in which a selected trained model is a high count model in the first application example of the second embodiment.

By the reconstruction function 751, the processing circuitry 75 inputs the acquired data to the selected trained model and outputs a reconstructed image data. FIG. 11 is a view showing an example of processing LCRecon in this step in a case in which the selected trained model is a low count model and processing HCRecon in this step in a case in which the selected trained model is a high count model.

If the acquisition time is short, the selected trained model is a low count model. In this case, the acquired data is acquired data of low count (to be referred to as low count data hereinafter). At this time, as shown in FIG. 11, by the reconstruction function 751, the processing circuitry 75 inputs the low count data to the low count model, thereby generating a reconstructed image data. In addition, if the acquisition time is long, the selected trained model is a high count model. In this case, the acquired data is acquired data of high count (to be referred to as high count data hereinafter). At this time, as shown in FIG. 11, the processing circuitry 75 inputs the high count data to the high count model, thereby generating a reconstructed image data. The processing circuitry 75 outputs the generated reconstructed image to the display 73. Note that the processing circuitry 75 may execute various kinds of image processing for the generated reconstructed image by the image processing function 752.

According to the above-described arrangement and operation, the following effects can be obtained in addition to the effects of the first embodiment.

According to the medical information processing apparatus in the PET apparatus 100 of this application example, a trained model to which a function is imparted to directly output a reconstructed image (PET image) concerning acquired data based on the data acquired by imaging (PET imaging) for the object P, and which is learned using raw data generated by a radiation physics simulator using a numerical phantom and the numerical phantom is stored, the acquired data is acquired, and the acquired data is input to the trained model, thereby generating a reconstructed image (PET image). The trained model stored in the medical information processing apparatus can incorporate various kinds of corrections concerning generation of the reconstructed image (PET image) in learning of the trained model generation processing 98 based on the raw data and the numerical phantom.

In addition, according to the medical information processing apparatus of this application example, a plurality of trained models are stored in accordance with an imaging condition including at least one of the count of gamma rays concerning acquired data, the count rate of gamma rays, and a nuclide name concerning generation of gamma rays, a trained model corresponding to the imaging condition (scan condition) is selected, based on the imaging condition in imaging, from the plurality of trained models stored in the memory 74 (storage unit), and the acquired data is input to the selected trained model, thereby generating a reconstructed image (PET image).

In addition, according to the medical information processing apparatus of this application example, it is possible to store a trained model corresponding to the geometrical arrangement of a plurality of detectors (gamma ray detectors 17) concerning acquisition of data. Additionally, according to the medical information processing apparatus of this application example, a plurality of trained models are stored in accordance with the application purpose of a reconstructed image (PET image), a trained model corresponding to the application purpose is selected, based on the application purpose, from the plurality of trained models stored in the memory 74 (storage unit), and the acquired data is input to the selected trained model, thereby generating a reconstructed image (PET image).

As described above, according to the medical information processing apparatus of this application example, the trained model generated in the first embodiment already has the function of correcting the influence of the geometrical arrangement of the gamma ray detectors 17, the detection efficiency, and the detector gap. For this reason, according to the medical information processing apparatus, a PET image can be generated without performing these corrections when reconstructing the PET image for acquired data. Accordingly, for example, these corrections are unnecessary in the reconstruction processing, and the examination efficiency can be improved. In addition, according to the medical information processing apparatus of this application example, it is possible to execute the reconstruction processing while selectively using the trained model in accordance with an imaging condition, a detector condition, and the application purpose of a PET image. For this reason, according to the medical information processing apparatus, it is possible to generate a reconstructed image suitable for the imaging condition, the detector condition, and the application purpose of a PET image. For example, according to the medical information processing apparatus of this application example, it is possible to generate a reconstructed image using a trained model suitable for reconstruction for a diagnostic image or a trained model suitable for simple reconstruction for imaging confirmation in accordance with a requirement of the operator.

Second Application Example

Figure 12:
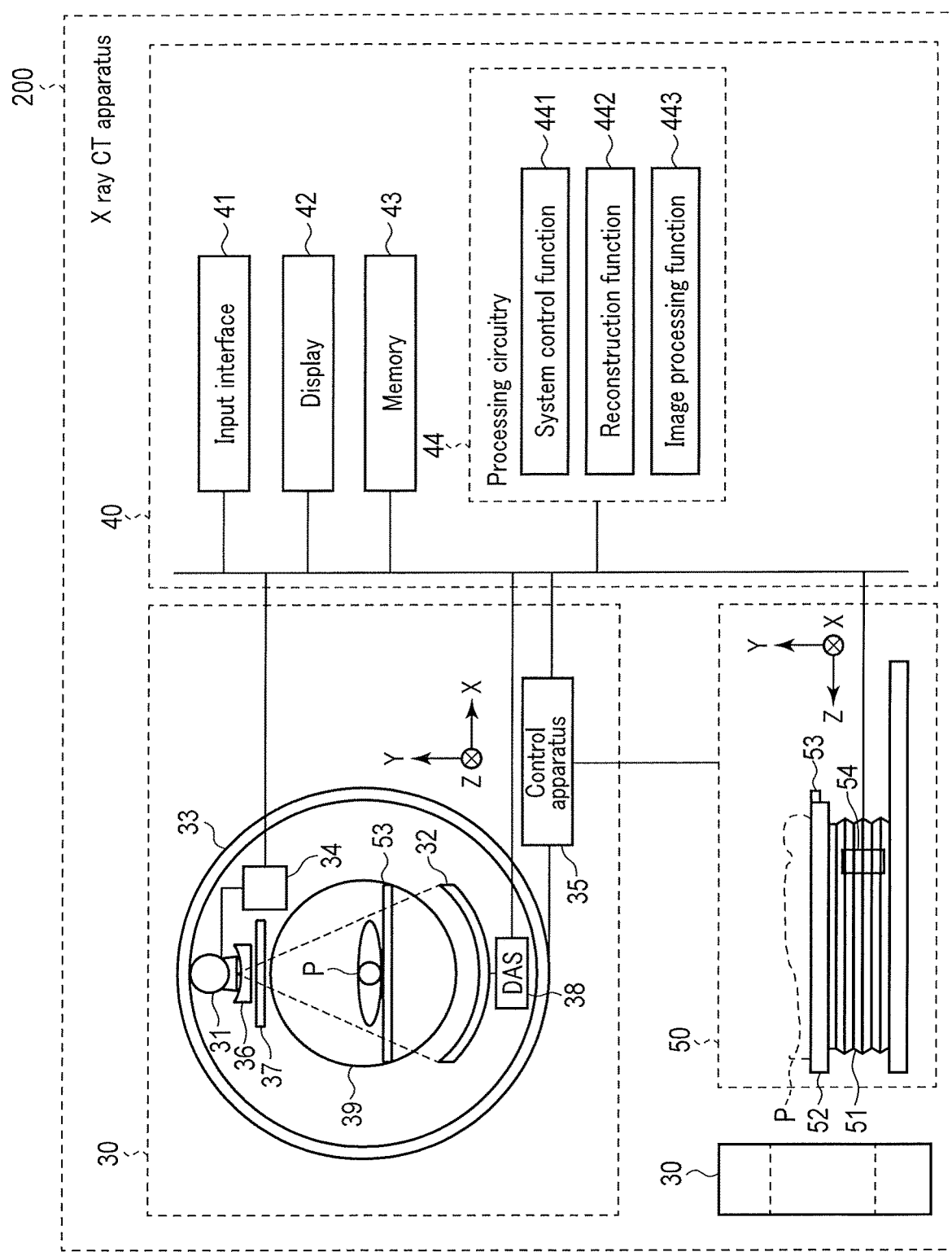
FIG. 12 is a view showing an example of the arrangement of an X-ray computed tomography (X-ray CT) apparatus in the second application example of the second embodiment.

The overall arrangement of an X-ray CT apparatus 200 according to this application example will be described with reference to FIG. 12. FIG. 12 is a view showing an example of the arrangement of the X-ray CT apparatus 200. As shown in FIG. 12, the X-ray CT apparatus 200 includes a CT gantry (data acquisition unit) 30, the couch 50, and a console 40. The medical information processing apparatus according to this application example includes a plurality of constituent elements in the console 40. Note that the medical information processing apparatus according to this application example may include the CT gantry 30. Note that FIG. 12 shows a plurality of CT gantries 30 for the descriptive convenience.

As the X-ray CT apparatus 200, there are various types such as a third generation CT and a fourth generation CT, and any type can be used as this application example. Here, the third generation CT is of a Rotate/Rotate-Type in which an X-ray tube 31 and an X-ray detector 32 integrally rotate around the object P. In the fourth generation CT, a number of X-ray detection elements arrayed in a ring shape are fixed to the CT gantry 30. The fourth generation CT is of a Stationary/Rotate-Type in which only the X-ray tube 31 rotates around the object P. Note that hardware that generates X-rays is not limited to the X-ray tube 31 shown in FIG. 12. For example, in place of the X-ray tube 31, a fifth generation system may be used to generate X-rays. The fifth generation system includes a focus coil, a deflection coil, and a target ring. The focus coil converges an electron beam generated from an electron gun. The deflection coil electromagnetically deflects the electron beam. The target ring is, arranged to surround a half circumference of the object P. The target ring generates X-rays when the deflected electron beam collides against it.

The geometrical arrangement of the plurality of X-ray detection elements in the X-ray CT apparatus 200 according to this application example, that is, the geometrical arrangement of the X-ray detector 32 has a structure in which a plurality of X-ray detection element arrays each including a plurality of X-ray detection elements arranged in the channel direction are arranged in the slice direction (column direction) (to be referred to as a two-dimensional structure hereinafter), as shown in FIG. 12. At this time, a memory 43 stores at least one trained model to which a detector condition including the geometrical arrangement of the two-dimensional structure and an imaging condition (scan condition) are attached.

To make a detailed description, the memory 43 is assumed to store a trained model (to be referred to as a high energy model hereinafter) to which an imaging condition including a high voltage is attached, and a trained model (to be referred to as a low energy model hereinafter) to which an imaging condition including a low voltage is attached. Note that the memory 43 may store a trained model to which an imaging condition including a tube current, a scan method, and the number of views used to reconstruct a CT image is attached.

The trained model according to this application example is assumed to be a machine learning model for which CT reconstruction learning has been executed using a numerical phantom and raw data corresponding to data output from data acquisition circuitry (to be referred to as a DAS (Data Acquisition System) hereinafter) 38.

Note that the trained model according to this application example may be a machine learning model for which CT reconstruction learning has been executed using a numerical phantom and raw data corresponding to projection data obtained by performing various kinds of preprocessing for data output from the DAS 38. Examples of preprocessing are logarithmic transformation processing, offset correction processing, sensitivity correction processing between channels, and beam hardening correction. In this case, the trained model incorporates various kinds of corrections concerning the preprocessing. At this time, the X-ray CT apparatus 200 has a preprocessing function (preprocessing unit) of executing preprocessing in processing circuitry 44. In addition, the trained model according to this application example may be a machine learning model for which CT reconstruction learning has been executed using a numerical phantom and raw data corresponding to data (to be referred to as pure raw data hereinafter) output from the X-ray detector 32. In this case, the trained model incorporates various kinds of correction processing concerning preprocessing and various kinds of processing contents executed by the DAS 38. At this time, the DAS 38 in the X-ray CT apparatus 200 is unnecessary.

The CT gantry 30 is a scan apparatus having an arrangement for executing X-ray CT imaging (to be also referred to as X-ray CT scan) for the object P. The object P as the target of X-ray CT imaging is placed on the couch 50. The couch 50 is a conveyance apparatus configured to positon the object P. The console 40 is a computer that controls the CT gantry 30. For example, the CT gantry 30 and the couch 50 are installed in a CT examination room. In addition, the console 40 is installed in a control room next to the CT examination room. The CT gantry 30, the couch 50, and the console 40 are connected by wire or wirelessly to be communicable with each other. Note that the console 40 need not always be installed in the control room. For example, the console 40 may be installed in the same room together with the CT gantry 30 and the couch 50. In addition, the console 40 may be incorporated in the CT gantry 30.

As shown in FIG. 12, the CT gantry 30 includes the X-ray tube 31, the X-ray detector 32, a rotating frame 33, an X-ray high voltage device 34, a control device 35, a wedge 36, a collimator 37, and the DAS 38.

The X-ray tube 31 irradiates the object P with X-rays. More specifically, the X-ray tube 31 includes a cathode that generates thermoelectrons, an anode that receives the thermoelectrons emitted from the cathode and generates X-rays, and a vacuum tube that holds the cathode and the anode. The X-ray tube 31 is connected to the X-ray high voltage device 34 via a high voltage cable. A tube voltage is applied across the cathode and the anode by the X-ray high voltage device 34. When the tube voltage is applied, thermoelectrons are emitted from the cathode to the anode. When the thermoelectrons are emitted from the cathode to the anode, a tube current flows. By the application of the high voltage from the X-ray high voltage device 34 and supply of a filament current, the thermoelectrons are emitted from the cathode (filament) to the anode (target). When the thermoelectrons collide against the anode, X-rays are generated. For example, as the X-ray tube 31, there is a rotary anode type X-ray tube that generates X-rays by irradiating a rotating anode with thermoelectrons.

The X-ray detector 32 detects the X-rays emitted from the X-ray tube 31 and transmitted through the object P. The X-ray detector 32 outputs an electrical signal corresponding to the dose of detected X-rays to the DAS 38. The X-ray detector 32 has a two-dimensional structure. The X-ray detector 32 is, for example, a detector of an indirect conversion type. The detector of an indirect conversion type includes, for example, a grid, a scintillator array, and an optical sensor array. The scintillator array includes a plurality of scintillators. The scintillator includes a scintillator crystal that outputs light of a light amount corresponding to an incident X-ray amount. The grid is arranged on the side of the X-ray incident surface of the scintillator array. The grid includes an X-ray shield plate that absorbs scattered X-rays. Note that the grid is sometimes called a collimator (a one-dimensional collimator or a two-dimensional collimator). The optical sensor array has a function of converting light output from the scintillator array into an electrical signal in accordance with the amount of the light. As the optical sensor, for example, a photodiode, a photomultiplier, or the like is used. Note that the X-ray detector 32 may be a detector of a direct conversion type. The detector of the direct conversion type includes a semiconductor element that converts incident X-rays into an electrical signal. The X-ray detector 32 is an example of an X-ray detection unit.

The rotating frame 33 is an annular frame. The annular frame supports the X-ray tube 31 and the X-ray detector 32 such that they can rotate about a rotation axis (Z-axis). More specifically, the rotating frame 33 makes the X-ray tube 31 and the X-ray detector 32 face each other and supports them. The rotating frame 33 is supported by a fixed frame (not shown) so as to be rotatable about the rotation axis. The rotating frame 33 is rotated about the rotation axis by the control device 35. Accordingly, the rotating frame 33 rotates the X-ray tube 31 and the X-ray detector 32 about the rotation axis. The rotating frame 33 receives power from the driving mechanism of the control device 35, and rotates about the rotation axis at an almost constant angular velocity. A field of view (FOV) is set on an opening portion 39 of the rotating frame 33. The rotating frame 33 is an example of a rotation unit. Note that in this application example, the rotation axis of the rotating frame 33 in a non-tilting state or the longitudinal direction of the couch top 53 of the couch 50 is defined as the Z-axis direction. Additionally, in this application example, an axial direction that is orthogonal to the Z-axis direction and level with respect to the floor surface is defined as an X-axis direction. Additionally, in this application example, an axial direction that is orthogonal to the Z-axis direction and perpendicular to the floor surface is defined as a Y-axis direction.

The X-ray high voltage device 34 includes a high voltage generation device and an X-ray control device. The high voltage generation device includes electrical circuitry such as a transformer and a rectifier. The high voltage generation device generates a high voltage to be applied to the X-ray tube 31 and a filament current to be supplied to the X-ray tube 31. The X-ray control device controls an output voltage according to the X-rays emitted from the X-ray tube 31. Note that the high voltage generation device may be of a transformer type or an inverter type. In addition, the X-ray high voltage device 34 may be provided on the rotating frame 33 in the CT gantry 30. Note that the X-ray high voltage device 34 may be provided on the fixed frame (not shown) in the CT gantry 30. The X-ray high voltage device 34 is an example of an X-ray high voltage unit.

The wedge 36 is a filter configured to adjust the dose of X-rays with which the object P is irradiated. More specifically, the wedge 36 attenuates X-rays such that the dose of the X-rays emitted from the X-ray tube 31 to the object P obtains a predetermined distribution. For example, as the wedge 36, a metal plate of aluminum or the like such as a wedge filter or a bow-tie filter is used. The metal plate is processed in advance to have a predetermined target angle or a predetermined thickness.

The collimator 37 limits the irradiation range of the X-rays transmitted through the wedge 36. The collimator 37 slidably supports a plurality of lead plates that shield X-rays. The collimator 37 adjusts the form of a slit formed by the plurality of lead plates. Note that the collimator 37 is sometimes called an X-ray diaphragm.

The DAS 38 reads, from the X-ray detector 32, an electrical signal corresponding to the dose of X-rays detected by the X-ray detector 32. The DAS 38 amplifies the read electrical signal. The DAS 38 integrates the amplified electrical signal for a view period. The DAS 38 thus acquires detection data having a digital value corresponding to the dose of X-rays for the view period. The DAS 38 is implemented by, for example, an ASIC or the like including a circuit element capable of generating detection data. The detection data is transferred to the console 40 via a noncontact data transmission device or the like. The noncontact data transmission device includes a transmitter provided on the rotating frame 33, and a receiver provided on the non-rotating portion (for example, the fixed frame (not shown)) of the CT gantry 30. The transmitter includes a light-emitting diode (LED). The receiver includes a photodiode. The transmitter transmits detection data to the receiver via the light-emitting diode. The receiver receives the detection data via the photodiode. The receiver transmits the received detection data to the console 40. The noncontact data transmission device thus transmits the detection data to the console via optical communication. Note that the detection data transmission method from the rotating frame 33 to the non-rotating portion of the CT gantry 30 is not limited to the above-described optical communication, and any method can be employed as long as it is noncontact data transmission.

The control device 35 controls the X-ray high voltage device 34 or the DAS 38 to execute X-ray CT imaging in accordance with a system control function 441 of the processing circuitry 44 in the console 40. The control device 35 includes processing circuitry with a CPU, an MPU, or the like, and a driving mechanism such as a motor and an actuator. The processing circuitry includes, as hardware resources, a processor such as a CPU, and memories such as a ROM and a RAM. In addition, the control apparatus 35 may be implemented by an ASIC, an FPGA, or the like. The control apparatus 35 may be implemented by a complex programmable logic device, a simple programmable logic device, or the like. The control apparatus 35 has a function of receiving an input signal from the console 40 or the input interface 41 attached to the CT gantry 30 and controlling the operations of the CT gantry 30 and the couch 50.

For example, the control device 35 performs control of receiving an input signal and rotating the rotating frame 33, control of tilting the CT gantry 30, control of operating the couch 50 and the couch top 53, and the like. Note that the control of tilting the CT gantry 30 is implemented when, for example, the control device 35 rotates the rotating frame 33 about an axis parallel to the X-axis direction based on the information of a tilt angle input by the input interface 41 attached to the CT gantry 30. Note that the control device 35 may be provided on the CT gantry 30 or may be provided on the console 40. The control device 35 is an example of a gantry control unit.

The couch 50 includes the base 51, the support frame 52, the couch top 53, and the couch driving device 54. The base 51 is installed on the floor surface of the CT examination room. An arrangement and operation concerning the base 51, the support frame 52, the couch top 53, and the couch driving device 54 are similar to those in the first application example, and a description thereof will be omitted.

The console 40 includes an input interface (input unit) 41, a display (display unit) 42, the memory (storage unit) 43, and the processing circuitry (processing unit) 44. Data communication between the input interface 41, the display 42, the memory 43, and the processing circuitry 44 is performed, for example, via a wired bus or wirelessly.

The input interface 41 accepts various kinds of input operations from the operator. The input interface 41 converts an accepted input operation into an electrical signal. The input interface 41 outputs the converted electrical signal to the processing circuitry 44. The input interface 41 supplies an output signal from an input device to the processing circuitry 44 via the bus. More specifically, the input interface 41 inputs an imaging condition and the like in accordance with an instruction of the operator before execution of CT scan for the object P. An input device serving as an implementation means of the input interface 41 is similar to that in the first embodiment, and a description thereof will be omitted.

The display 42 displays various kinds of information under the control of the system control function 441 of the processing circuitry 44. The display 42 displays, for example, a GUI concerning input of an imaging condition and the like. The display 42 displays a CT image generated by a reconstruction function 442 of the processing circuitry 44 and a medical image generated by an image processing function 443. A display device serving as an implementation means of the display 42 is similar to that in the first embodiment, and a description thereof will be omitted.

The memory 43 stores various kinds of conditions input via the input interface 41, information, programs corresponding to a plurality of functions executed by the processing circuitry 44, a CT image generated by the reconstruction function 442, and a medical image generated by the image processing function 443. The memory 43 stores detection data output from the DAS 38 as acquired data in association with a view angle and a detection element number. The memory 43 stores a trained model corresponding to the geometrical arrangement of the plurality of detectors (X-ray detectors 32) concerning acquisition of data. That is, the memory 43 stores at least one trained model corresponding to a detector condition concerning the geometrical arrangement of the X-ray detector 32. The memory 43 stores a plurality of trained models in accordance with an imaging condition (scan condition) including at least one of a scan method concerning acquisition of data, the number of views used for reconstruction, a tube voltage, and a tube current. For example, the memory 43 store a high energy model and a low energy model together with an associated imaging condition, as described above. A storage device serving as an implementation means of the memory 43 is similar to that in the first embodiment, and a description thereof will be omitted.

The processing circuitry 44 controls the operation of the entire X-ray CT apparatus 200 in accordance with the electrical signal of an input operation output from the input interface 41. The processing circuitry 44 includes, as hardware resources, a processor such as a CPU, an MPU, or a GPU and memories such as a ROM and a RAM. The processing circuitry 44 executes the system control function 441, the reconstruction function 442, the image processing function 443, and the like by the processor that executes a program loaded into the memory. Note that the plurality of functions are not always implemented by the single processing circuitry. The processing circuitry may be formed by combining a plurality of independent processors, and the processors in the processing circuitry may execute the programs, thereby implementing the plurality of functions. The processing circuitry 44 that implements the system control function 441, the reconstruction function 442, and the image processing function 443 is an example of a system control unit, a reconstruction unit, and an image processing unit.

By the system control function 441, the processing circuitry 44 controls the X-ray high voltage device 34, the control device 35, the DAS 38, and the like to perform X-ray CT imaging.

By the reconstruction function 442, the processing circuitry 44 selects a trained model stored in the memory 43 in accordance with an imaging condition input via the input interface 41. Note that the processing circuitry 44 in the medical information processing apparatus receives the data from the CT gantry 30 (more specifically, the DAS 38) or the memory 43. The processing circuitry 44 inputs the data to the selected trained model. The processing circuitry 44 executes the trained model to which the data is input. The processing circuitry 44 executes the trained model, thereby generating a CT image as a reconstructed image data of the data. The processing circuitry 44 outputs the generated CT image to the display 42 and the memory 43.

By the image processing function 443, the processing circuitry 44 converts the data of the CT image generated by the reconstruction function 442 into sectional image data of an arbitrary section or rendering image data in an arbitrary viewpoint direction. The conversion is performed based on an input operation accepted from the operator via the input interface 41. For example, the processing circuitry 44 executes three-dimensional image processing such as volume rendering, surface volume rendering, pixel value projection processing, MPR processing, and CPR processing for the data of the CT image, thereby generating or rendering image data in an arbitrary viewpoint direction.

Note that the console 40 executes the plurality of functions by the single console, as described above. However, the plurality of functions may be executed by separate consoles. For example, the functions of the processing circuitry 44 such as the system control function 441, the reconstruction function 442, and the image processing function 443 may distributively be included in separate consoles.

Note that the technique according to this application example can be applied to both a medical X-ray CT apparatus of a single tube type and a medical X-ray CT apparatus of a so-called multi-tube type in which a plurality of pairs of X-ray tubes and detectors are provided on the rotary ring.

The overall arrangement of the X-ray CT apparatus 200 according to this application example has been described above. The processing procedure (to be referred to as CT reconstruction processing hereinafter) of reconstruction of a CT image in the X-ray CT apparatus 200 will be described below. The outline of the CT reconstruction processing is almost the same as the PET reconstruction processing, and will be described with reference to FIG. 10.

(CT Reconstruction Processing)
(Step Sc1)
The input interface 41 inputs an imaging condition concerning CT scan before execution of CT scan.
(Step Sc2)
The processing circuitry 44 executes CT scan for the object P in accordance with the imaging condition by the system control function 441, and receives acquired data. The processing circuitry 44 stores the acquired data in the memory 43.

(Step Sc3)

By the reconstruction function 442, the processing circuitry 44 selects a trained model to be used to reconstruct a CT image, based on the imaging condition, from a plurality of trained models stored in the memory 43. For example, if a low tube voltage is included in the imaging condition, the processing circuitry 44 selects a low energy model. If a high tube voltage is included in the imaging condition, the processing circuitry 44 selects a high energy model.

(Step Sc4)

By the reconstruction function 442, the processing circuitry 44 inputs the data to the selected trained model and outputs a reconstructed image as a CT image. For example, if CT scan is executed by a low tube voltage, the selected trained model is a low energy model. In this case, the acquired data is acquired data at the low tube voltage (to be referred to as low tube voltage data hereinafter). At this time, the processing circuitry 44 inputs the low tube voltage data to the low energy model, thereby generating a reconstructed image data. In addition, if CT scan is executed by a high tube voltage, the selected trained model is a high energy model. In this case, the acquired data is acquired data at the high tube voltage (to be referred to as high tube voltage data hereinafter). At this time, the processing circuitry 44 inputs the high tube voltage data to the high energy model, thereby generating a reconstructed image data. The processing circuitry 44 outputs the generated reconstructed image to the display 42. Note that the processing circuitry 44 may execute various kinds of image processing for the generated reconstructed image by the image processing function 443. Note that in this application example, reconstruction processing is executed while selectively using the trained model in accordance with the application purpose of a CT image, as in the first application example, and a description thereof will be omitted.

According to the above-described arrangement and operation, the following effects can be obtained in addition to the effects of the first embodiment.

According to the medical information processing apparatus in the X-ray CT apparatus 200 of this application example, a trained model to which a function is imparted to directly output a reconstructed image (CT image) concerning acquired data based on the data acquired by imaging (CT scan) for the object P, and which is learned using raw data generated by a radiation physics simulator using a numerical phantom and the numerical phantom is stored, the acquired data is acquired, and the acquired data is input to the trained model, thereby generating a reconstructed image (CT image). The trained model stored in the X-ray CT apparatus 200 can incorporate various kinds of corrections concerning generation of the reconstructed image (CT image) in learning of the trained model generation processing 98 based on the raw data and the numerical phantom.

In addition, according to the medical information processing apparatus of this application example, a plurality of trained models are stored in accordance with an imaging condition (scan condition) including at least one of a scan method concerning acquisition of data, the number of views used for reconstruction, a tube voltage, and a tube current, a trained model corresponding to the imaging condition is selected, based on the imaging condition in imaging, from the plurality of trained models stored in the memory 43 (storage unit), and the acquired data is input to the selected trained model, thereby generating a reconstructed image (CT image). In addition, according to the medical information processing apparatus of this application example, it is possible to store a trained model corresponding to the geometrical arrangement of a plurality of detectors (X-ray detectors) concerning acquisition of data.

Additionally, according to the medical information processing apparatus of this application example, a plurality of trained models are stored in accordance with the application purpose of a reconstructed image (CT image), a trained model corresponding to the application purpose is selected, based on the application purpose, from the plurality of trained models stored in the memory 43 (storage unit), and the acquired data is input to the selected trained model, thereby generating a reconstructed image (CT image).

As described above, according to the medical information processing apparatus of this application example, the trained model generated in the first embodiment already has the function of correcting the influence of the geometrical arrangement of the X-ray detectors 32, the detection efficiency, and the detector gap. For this reason, according to the medical information processing apparatus, a CT image can be generated without performing these corrections when reconstructing the CT image for acquired data. Accordingly, for example, these corrections are unnecessary in the reconstruction processing, and the examination efficiency can be improved. In addition, according to the medical information processing apparatus of this application example, it is possible to execute the reconstruction processing while selectively using the trained model in accordance with an imaging condition, a detector condition, and the application purpose of a CT image. For this reason, it is possible to generate a reconstructed image suitable for the imaging condition, the detector condition, and the application purpose of a CT image. For example, according to the medical information processing apparatus of this application example, it is possible to generate a reconstructed image using a trained model suitable for reconstruction for a diagnostic image or a trained model suitable for simple reconstruction for imaging confirmation in accordance with a requirement of the operator.

As application examples of the first embodiment, the second embodiment, the first application example, and the second application example, the technical idea of the medical information-processing apparatus 1 can also be implemented by installing programs concerning the training data generation processing 94, the trained model generation processing 98, and the reconstruction processing (PET reconstruction processing and CT reconstruction processing) in a computer such as a workstation and loading them into a memory. For example, the program configured to execute the training data generation processing 94 causes the computer to implement outputting an image corresponding to a numerical phantom and raw data in association with each other as training data used to generate a trained model to which a function is imparted to receive input of the image corresponding to the numerical phantom, acquire raw data generated based on the image corresponding to the numerical phantom and a predetermined scan condition, receive data acquired by scan for an object, and output a reconstructed image data concerning the data.

In addition, the program configured to execute the trained model generation processing 98 causes the computer to implement generating a trained model by learning a machine learning model using training data generated by the training data generation processing 94. Furthermore, the program configured to execute the reconstruction processing causes the computer to implement receiving data acquired by scan for an object, and outputting a reconstructed image data based on the data and a trained model that is trained by learning using raw data generated based on a numerical phantom and the numerical phantom, accepts the data as input data, and outputs a reconstructed image data corresponding to the data. The program capable of causing the computer to execute the method can also be stored in various kinds of portable storage media such as a magnetic disk, an optical disk, and a semiconductor memory and distributed.

As an application example of the first embodiment, if the technical idea of the medical information processing apparatus 1 is implemented by a cloud or the like, a server on the Internet includes, for example, the memory 7 and the processing circuitry 9 shown in the block diagram of FIG. 1. At this time, the training data generation processing 94 and the trained model generation processing 98 are implemented by installing the programs configured to execute these processes in the processing circuitry 9 of the server and executing the installed programs by the server. In addition, the input interface 3 and the display 5 are implemented on, for example, various kinds of terminals via a network.

According to the medical information processing apparatus of each of the above-described embodiments and application examples, it is possible to perform reconstruction processing in accordance with a trained model learned using raw data generated using a numerical phantom and the numerical phantom.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical information processing apparatus comprising:
    a memory; and
    processing circuitry configured to:
        receive raw data acquired by scan for an object; and
        output reconstructed image data based on the received raw data and a trained model that accepts the received raw data as input data and outputs reconstructed image data corresponding to the received raw data, wherein
    the trained model is trained by learning using raw data generated based on a numerical phantom and the numerical phantom,
    the memory is configured to store a plurality of trained models in accordance with a scan condition including at least one of a count of gamma rays concerning the received raw data, a count rate of the gamma rays, and a nuclide name concerning generation of the gamma rays, and
    the processing circuitry is configured to:
        receive a selection of a trained model corresponding to the scan condition from the plurality of trained models stored in the memory, based on the scan condition in the scan; and
        input the received raw data to the selected trained model, thereby generating the reconstructed image data.

2. The medical information processing apparatus according to claim 1, wherein the received raw data is formed by a detection event of gamma rays.

3. A medical information processing apparatus comprising:
    a memory; and
    processing circuitry configured to:
        receive raw data acquired by scan for an object; and
        output reconstructed image data based on the received raw data and a trained model that accepts the received raw data as input data and outputs reconstructed image data corresponding to the received raw data, wherein
    the trained model is trained by learning using raw data generated based on a numerical phantom and the numerical phantom,
    the memory is configured to store a plurality of trained models in accordance with a scan condition including at least one of a scan method concerning acquisition of the received raw data, a number of views used for reconstruction, a tube voltage, and a tube current, and
    the processing circuitry is configured to:
        receive a selection of a trained model corresponding to the scan condition from the plurality of trained models stored in the memory, based on the scan condition in the scan; and
        input the received raw data to the selected trained model, thereby generating the reconstructed image data.

4. The medical information processing apparatus according to claim 3, wherein
    the trained model corresponds to a geometrical arrangement of a plurality of detectors concerning acquisition of the received raw data.

5. The medical information processing apparatus according to claim 3, wherein the received raw data is formed by a detection event of gamma rays.

6. A medical information processing apparatus comprising:
    a memory; and
    processing circuitry configured to:
        receive raw data acquired by scan for an object; and
        output reconstructed image data based on the received raw data and a trained model that accepts the received raw data as input data and outputs reconstructed image data corresponding to the received raw data, wherein
    the trained model is trained by learning using raw data generated based on a numerical phantom and the numerical phantom,
    the memory is configured to store a plurality of trained models in accordance with an application purpose of the reconstructed image data, and
    the processing circuitry is configured to:
        receive a selection of a trained model corresponding to the application purpose from the plurality of trained models stored in the memory, based on the application purpose; and
        input the received raw data to the selected trained model, thereby generating the reconstructed image data.

7. A medical information processing apparatus comprising:
    a memory; and
    processing circuitry configured to:
        receive raw data acquired by scan for an object; and
        output reconstructed image data based on the received raw data and a trained model that accepts the received raw data as input data and outputs reconstructed image data corresponding to the received raw data, wherein the trained model is trained by learning using raw data generated based on a numerical phantom and the numerical phantom, and the memory is configured to store a plurality of trained models in accordance with a scan condition including at least one of a count of gamma rays concerning the received raw data, a count rate of the gamma rays, and a nuclide name concerning generation of the gamma rays.

8. A medical information processing apparatus comprising:

a memory; and processing circuitry configured to:

receive raw data acquired by scan for an object; and output reconstructed image data based on the received raw data and a trained model that accepts the received raw data as input data and outputs reconstructed image data corresponding to the received raw data, wherein the trained model is trained by learning using raw data generated based on a numerical phantom and the numerical phantom, and the memory is configured to store a plurality of trained models in accordance with a scan condition including at least one of a scan method concerning acquisition of the received raw data, a number of views used for reconstruction, a tube voltage, and a tube current.

9. A medical information processing apparatus comprising:

a memory; and processing circuitry configured to:

receive raw data acquired by scan for an object; and output reconstructed image data based on the received raw data and a trained model that accepts the received raw data as input data and outputs reconstructed image data corresponding to the received raw data, wherein the trained model is trained by learning using raw data generated based on a numerical phantom and the numerical phantom, and the memory is configured to store a plurality of trained models in accordance with an application purpose of the reconstructed image data.

10. A medical information processing apparatus, comprising:

a memory; and processing circuitry configured to:

receive data acquired by scan for an object, and output reconstructed image data based on the data and a trained model that accepts the data as input data and outputs reconstructed image data corresponding to the data, wherein the trained model is trained by learning using raw data generated based on a numerical phantom and the numerical phantom, the memory is configured to store a plurality of trained models in accordance with an application purpose of the reconstructed image data, and the processing circuitry is further configured to:

receive a selection of a trained model corresponding to the application purpose from the plurality of trained models stored in the memory, based on the application purpose, and input the data to the selected trained model, thereby generating the reconstructed image data.

* * * * *